US011305037B2

(12) United States Patent
O'Brien et al.

(10) Patent No.: US 11,305,037 B2
(45) Date of Patent: Apr. 19, 2022

(54) FACEMASK HAVING INTEGRATED MODULES

(71) Applicants: Patrick Damien O'Brien, Ennis (IE); Jez Noah Ali, Ennis (IE); Arthur Ali, Ennis (IE)

(72) Inventors: Patrick Damien O'Brien, Ennis (IE); Jez Noah Ali, Ennis (IE); Arthur Ali, Ennis (IE)

(*) Notice: Subject to any disclaimer, the term of this patent is extended or adjusted under 35 U.S.C. 154(b) by 0 days.

(21) Appl. No.: 17/112,982

(22) Filed: Dec. 5, 2020

(65) Prior Publication Data
US 2021/0086005 A1 Mar. 25, 2021

Related U.S. Application Data

(60) Provisional application No. 63/104,632, filed on Oct. 23, 2020.

(51) Int. Cl.
*A62B 18/02* (2006.01)
*A61L 27/48* (2006.01)
(Continued)

(52) U.S. Cl.
CPC ............... *A61L 27/48* (2013.01); *A61L 27/16* (2013.01); *A61L 27/20* (2013.01); *A61M 5/329* (2013.01);
(Continued)

(58) Field of Classification Search
CPC ... A62B 18/02; A62B 1823/025; A62B 18/10; A62B 9/006; A62B 7/10; A62B 18/08; A62B 23/02; A62B 18/086; A41D 13/11
See application file for complete search history.

(56) References Cited

U.S. PATENT DOCUMENTS 3,540,442 A 11/1970 Holloway
5,572,990 A 11/1996 Berlin
(Continued)

FOREIGN PATENT DOCUMENTS

CN 107174767 A 9/2017
CN 107405508 A 11/2017
(Continued)

OTHER PUBLICATIONS

Xu Z, Shen F, Li X, et al. Molecular and microscopic analysis of bacteria and viruses in exhaled breath collected using a simple impaction and condensing method. PLoS One. 2012;7(7):e41137. doi:10.1371/journal.pone.0041137.
(Continued)

*Primary Examiner* — Margaret M Luarca
(74) *Attorney, Agent, or Firm* — Allen F. Bennett; Bennett Intellectual Property

(57) ABSTRACT

A facemask includes integrated actuating modules having sensors and other mechanisms. The facemask has one or more sockets into which various modules may be inserted. The facemask itself or the modules may include air filters and check valves to regulate airflow along or through the various modules. The modules may detect various substances either in the ambient air or the air exhaled by the wearer. The facemask also includes modules for measuring pulmonary and/or cardiovascular exertion, lung capacity and other physiological metrics. Other modules may provide supplements, vitamins or other substances such as tobacco smoke or vapor from vaporizers to the wearer. The modules may include microcontrollers in wireless communication with software applications on electronic devices so that the facemask may also serve as a cellular phone.

15 Claims, 13 Drawing Sheets

(51) Int. Cl.

| | |
|---|---|
| *A61L 27/16* | (2006.01) |
| *A61L 27/20* | (2006.01) |
| *C08L 5/08* | (2006.01) |
| *C08L 33/12* | (2006.01) |
| *A62B 9/00* | (2006.01) |
| *A62B 18/10* | (2006.01) |
| *A62B 23/02* | (2006.01) |
| *A61M 5/32* | (2006.01) |
| *A61F 2/44* | (2006.01) |

(52) U.S. Cl.
CPC .............. *A62B 9/006* (2013.01); *A62B 18/02* (2013.01); *A62B 18/10* (2013.01); *A62B 23/025* (2013.01); *C08L 5/08* (2013.01); *C08L 33/12* (2013.01); *A61F 2002/4435* (2013.01); *A61L 2430/38* (2013.01); *A61M 2210/02* (2013.01)

(56) References Cited

U.S. PATENT DOCUMENTS

| | | | |
|---|---|---|---|
| 8,574,331 B2 | 11/2013 | Bangera et al. | |
| 9,169,521 B1* | 10/2015 | Rajagopal | B01L 3/5027 |
| 2012/0065483 A1* | 3/2012 | Chung | A01K 11/006 |
| | | | 600/310 |
| 2018/0000173 A1 | 1/2018 | Tsaur et al. | |
| 2018/0078798 A1 | 3/2018 | Fabian et al. | |
| 2020/0268995 A1* | 8/2020 | Shin | A61M 16/06 |

FOREIGN PATENT DOCUMENTS

| | | |
|---|---|---|
| DE | 102016223182 A1 | 5/2018 |
| DE | 102018009777 A1 | 6/2020 |
| EP | 3437984 B1 | 6/2019 |
| KR | 20110106728 A | 9/2011 |
| KR | 101474519 B1 | 12/2014 |
| KR | 101940383 B1 | 1/2019 |
| KR | 200489541 Y1 | 7/2019 |
| KR | 102030473 B1 | 10/2019 |
| KR | 102157371 B1 | 10/2020 |
| TW | 201350167 A | 8/2012 |
| TW | I707128 B | 4/2020 |

OTHER PUBLICATIONS

Khoubnasabjafari M, Jouyban-Gharamaleki V, Ghanbari R, Jouyban A. Exhaled breath condensate as a potential specimen for diagnosing COVID-19. Bioanalysis. 2020;12(17):1195-1197. doi:10.4155/bio-2020-0083.

Sukul, P., Schubert, J.K., Zanaty, K. et al. Exhaled breath compositions under varying respiratory rhythms reflects ventilatory variations: translating breathomics towards respiratory medicine. Sci Rep 10, 14109 (2020). https://doi.org/10.1038/S41598-020-70993-0.

* cited by examiner

FACEMASK HAVING INTEGRATED MODULES

CROSS-REFERENCE TO RELATED APPLICATIONS

This application claims priority to U.S. Provisional Application Ser. No. 62/104,632 filed on Oct. 23, 2020, the contents of which are hereby incorporated in their entirety.

STATEMENT REGARDING FEDERALLY SPONSORED RESEARCH OR DEVELOPMENT

Not Applicable

NAMES OF PARTIES TO A JOINT RESEARCH AGREEMENT

Not Applicable

REFERENCE TO SEQUENCE LISTING, A TABLE, OR A COMPUTER PROGRAM LISTING APPENDIX SUBMITTED ON A COMPACT DISC AND INCORPORATION-BY-REFERENCE OF THE MATERIAL

Not Applicable.

COPYRIGHT NOTICE

Not Applicable

BACKGROUND OF THE INVENTION

Field of the Invention

The present invention relates to a facemask having integrated modules. More particularly, the invention relates to a facemask having one or more sockets into which various modules may be inserted for detecting airborne substances and/or aerosol delivery of chemical compositions.

Description of the Related Art

The COVID-19 pandemic stemming from a new strain of coronavirus has had a substantial impact on society and daily life since early 2020. Despite having a seemingly low mortality rate, it is highly contagious and has already caused millions of deaths. One of the most effective methods of slowing the spread of this disease is the wearing of face masks covering the nose and mouth. This simple act reduces both the likelihood of a person inhaling the coronavirus and the likelihood of an infected person spreading the disease to others. As a result, face masks have become an everyday part of life, being worn whenever one leaves the house. This has produced a rapidly growing market for all types of customized face masks. Facemasks have now become a fashion accessory, a means for espousing personal views on societal issues or a favorite sports team. In addition, facemasks have been developed to include specialized features to provide better protection than facemasks made from breathable fabric.

There are drawbacks to wearing facemasks. Over time, they become uncomfortable, and they can make breathing more difficult. They must be removed for a person to ingest food, vitamins and supplements. One must also remove the mask to smoke or use a vaporizer. They also muffle words spoken by the wearer, making communication more difficult. This is exacerbated when the wearer attempts to speak over a telephone.

Many recent modifications to facemasks are problematic or fail to address problems associated with COVID-19. For example, many facemasks are designed to filter incoming, inhaled air. However, during a pandemic the primary purpose of wearing a facemask is to prevent air exhaled from the wearer from contaminating others around him or her. Some facemasks include one-way exit valves that make the facemask more comfortable for the wearer. They make breathing easier and prevent fogging of glasses. However, they all but defeat the purpose of preventing spread of pathogens from the wearer.

A separate, seemingly unrelated, popular trend is the use of wearable "smart" technology, such as the iwatch® and the Fitbit®. These devices are conveniently worn on the wrist and provide their users with an abundance of data regarding their physical condition in real time. This allows users to monitor their heart rate, steps taken and other data that may be used to determine the amount of exercise or physical exertion a person experiences throughout the day.

Unfortunately, these devices are remarkably inaccurate. Heart rate measurements by these devices can be as little as 34% accurate. Their methods of measuring steps taken by a wearer are frequently as much as 50% inaccurate. Thus, they are unreliable for accurately tracking the amount of physical exertion a person experiences throughout the day. Even worse, they can fail to alert a user when he or she is dangerously over-exerted. These devices are also incapable of detecting cardiovascular exertion or measuring the presence or absence of any chemicals or other objects inside a person.

The above-described deficiencies of today's systems are merely intended to provide an overview of some of the problems of conventional systems, and are not intended to be exhaustive. Other problems with the state of the art and corresponding benefits of some of the various non-limiting embodiments may become further apparent upon review of the following detailed description.

In view of the foregoing, it is desirable to provide a facemask that is more accommodating to wearers who wish to ingest substances without removing their mask. It is also desirable to provide wearable smart technology that accurately measures the wearer's physical exertion, and also is capable of detecting the presence or absence of chemicals or objects inside the wearer.

BRIEF SUMMARY OF THE INVENTION

Disclosed is a facemask having integrated sensing and actuation modules. A variety of different modules may be used to sense various physical characteristics and attributes of the wearer of the mask. Additional modules may be used to deliver various chemical compositions which are inhaled by the wearer.

In one embodiment, a facemask having integrated modules comprises a panel formed from substantially airtight fabric configured to cover the mouth and nose of a wearer. The panel has an inside surface and an outside surface, an air permeable first socket in the panel, a first module removably inserted into the first socket, a first check valve restricting airflow through the first socket to an outward direction, and a first filter substantially coextensive with the air permeable first socket and positioned outward relative to the first module.

In another embodiment, the first module detects a presence of a communicable disease in air flowing through the first socket and includes a thermometer.

In another embodiment, the facemask includes a view screen on the facemask displaying the temperature measured by the thermometer, and indicating whether the first module has detected the presence of the communicable disease.

In another embodiment, the facemask has a microphone on the inside surface of the panel, at least one earpiece having a speaker, and a microcontroller providing wireless communication. The facemask also includes a GPS tracking chip. The microcontroller periodically transmits location data obtained from the GPS tracking chip once the first module has detected the presence of the communicable disease.

In another embodiment, the facemask includes a heart rate monitor.

In another embodiment, a second module is removably inserted into an air permeable second socket, a second filter is substantially coextensive with the second socket, and a second check valve restricts airflow through the second socket to an inward direction.

In another embodiment, the first check valve is integrated into the first module and the second check valve is integrated into the second module.

In another embodiment, the socket is on the inside of the panel, and the inside surface of the panel includes a saliva sensor, at least one airflow sensor, and an optical head mounted display.

In another embodiment, the module comprises an upper section formed from the first filter integrated into an outer layer, an inner moisture capturing layer comprising a plurality of longitudinal hydrophobic ridges, the first check valve located between the outer layer and the inner moisture capturing layer, wherein each of the ridges includes a heat sink fin extending from inside the hydrophobic ridge and through the first check valve and the outer layer. The outer layer has a lower check valve limiting airflow to an inward direction through the lower section, and an inner layer comprising a water-soluble inhalable medicament.

In another embodiment, the facemask includes two earpieces, each having a lip forming a curved channel configured to fit over a wearer's ear, thereby securing the facemask over the wearer's mouth and nose.

It is therefore an object of the present invention to provide a facemask having integrated smart technology to provide a smart inhalation mask.

These and other objects and advantages of the present invention will become apparent from a reading of the attached specification and appended claims. There has thus been outlined, rather broadly, the more important features of the invention in order that the detailed description thereof that follows may be better understood, and in order that the present contribution to the art may be better appreciated. There are features of the invention that will be described hereinafter and which will form the subject matter of the claims appended hereto.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
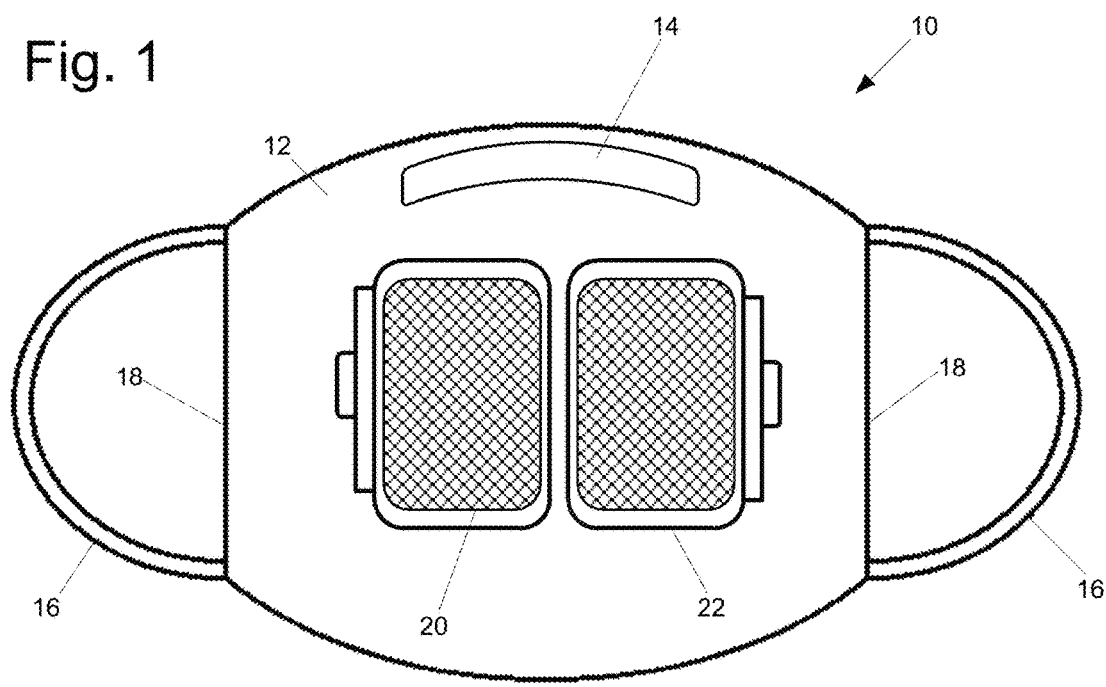
FIG. 1 is an outside view of a facemask having integrated modules in accordance with the principles of the invention.

The invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

The disclosed subject matter is described with reference to the drawings, wherein like reference numerals are used to refer to like elements throughout. In the following description, for purposes of explanation, numerous specific details are set forth in order to provide a thorough understanding of the various embodiments of the subject disclosure. It may be evident, however, that the disclosed subject matter may be practiced without these specific details. In other instances, well-known structures and devices are shown in block diagram form in order to facilitate describing the various embodiments herein. Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

Unless otherwise indicated, all numbers expressing quantities of ingredients, dimensions, reaction conditions and so forth used in the specification and claims are to be understood as being modified in all instances by the term "about". The term "a" or "an" as used herein means "at least one" unless specified otherwise. In this specification and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

As used herein, the term "socket" refers to a region of a facemask that provides removable attachment of a module to the facemask. In some embodiments, the socket comprises a pocket formed by fabric or other material attached on three sides to a panel of a facemask, where a module may be slid into the pocket formed. Other embodiments have sockets formed by opposing slots into which tongues along the sides of the modules slide into and optionally snapped into. Those skilled in the art will appreciate that there are a wide variety of methods for removably attaching modules to the fabric of a panel of a facemask. Sockets are generally configured to allow air to pass through the module within the socket and through the facemask. Regions of a socket may be configured to not allow air to pass through certain regions of a socket and/or module. Optionally, some modules may fit entirely within a socket or only partially within it. Sockets may also optionally include a USB port or similar device to allow a module to be in communication with another electronic device integrated into the mask.

The panels that form the major portion of the mask are generally made from a flexible fabric as are well known in the art. The panels may be formed from fabrics that are impermeable to air or which only provide very limited airflow through them such that most air inhaled and exhaled by a wearer is channeled through the sockets and any modules within the sockets. For example, relatively thick cotton masks may be formed that allow some airflow through them, but are sufficiently thick and tightly woven such that air flows more easily through the sockets and modules of the facemask. The sockets and modules shown herein are typically ovular and rectangular, but those skilled in the art will appreciate that they may take other forms. For example, modules could be circular or have other configurations. It is typically desirable for the modules to be relatively flat, but some modules may have other configurations.

Throughout this specification, the "inside" of a facemask refers to the side of a facemask facing the wearer while it is being worn. "Outside" of a facemask refers to the side of a facemask facing away from the wearer and viewable by others. "Inside" and "outside" are used in the same way to identify sides of the modules themselves, and are also used to refer to relative directions in relative orientations of various components of the modules with respect to each other. Similarly, and "inward direction" refers to air flowing from the outside to the inside of the facemask while "outward direction" refers to air flowing in the opposite direction, from the inside to the outside of the facemask. Air being inhaled by a wearer is flowing in an inward direction while air exhaled from the wearer will flow in an outward direction. Typically, inhaled and out held air will flow through various modules, depending on the orientation of check valves in front of or behind the modules.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure. For example, different embodiments will show different types of sockets, different types of modules, and/or different devices integrated into the facemask. It is explicitly contemplated that all of these devices can be combined in different ways unless explicitly stated otherwise herein, or unless the context in which they are described makes clear that certain components are incompatible.

Disclosed is a facemask configured to comfortably fit over the mouth and nose of a wearer. The facemask may include elastic bands to hold the mask in place by wrapping around the ears or head of the wearer. The mask includes one or more sockets configured to removably and securely retain modules used to regulate inflow and outflow of air across the mask from the wearer to the ambient environment. The modules may also be used to measure air flow, force, air pressure, air volume, temperature and the presence or absence of a variety of substances either flowing into or out of the facemask. Either the facemask and/or the modules may include check valves that govern whether or not sensors within the modules monitor air entering or leaving the wearer's pulmonary tract. The modules integrated into the mask can detect anomalies in the air and in air pressure flagging up any airborne viruses and immediately registering them and the data to your smart device and also optionally to a physician's, spouse's, employer's and/or family's computer network. By using check valves restricting airflow to a single direction, the module detecting substances in exhaled air is not exposed to the ambient air, which may otherwise result in a false positive reading by the sensor.

FIG. 1 shows a facemask 10 having integrated modules in accordance with principles of the invention. The facemask 10 has a panel 12 configured to fit over the mouth and nose of a wearer. The facemask 10 may include one or more rigid or semirigid supports 14 which may be adjusted to more comfortably and securely fit over a wearer's nose. The facemask 10 includes two elastic bands 16 extending from each lateral side 18 of the panel 12 which may be placed over the wearer's ears to secure the facemask 10 in place. Optionally, two or more bands may extend from either lateral side 18 of the panel 12 and extend entirely around the wearer's head. Those skilled in the art will appreciate that there are a variety of ways to secure the panel 12 of the facemask 10 in the correct location over the wearer's mouth and nose. The present invention contemplates any such suitable manner of securing the panel 12 in the correct location.

The facemask 10 includes two separate sockets, an exhaling socket 20 and an inhaling socket 22 placed symmetrically about the center of the panel 12. The sockets 20 and 22 of this embodiment are shown positioned side-by-side. Optionally, the sockets 20 and 22 may be of different sizes and may be placed in different locations and different orientations relative to one another. For example, it may be desirable for sockets to be positioned above and below each other as opposed to side-by-side. Sockets 20 and 22 are also shown as being substantially rectangular. Optionally, the sockets may be circular or have a different configuration.

The sockets 20 and 22 include filters 24 and 26. These filters may be selected to prevent transmission of particles of a predetermined size and may optionally be interchangeable with other filter types. The sockets are shown in more detail in FIG. 2. Sockets 20 and 22 are both pockets formed from smaller panels of material affixed along three sides to the exterior side of the panel 12, such that a module may be removably inserted from the lateral side of the socket. The exhaling socket 20 includes a check valve 28, i.e. a one-way valve, in the panel 12 that allows airflow in an outward direction relative to the wearer's face. Conversely, the inhaling socket 22 includes a check valve 30 in the panel 12 that allows airflow in an inward direction toward the wearer's nose and mouth. Thus, when the wearer inhales, the air inhaled travels through the check valve 30. When the wearer exhales, the air travels through the check valve 28. This allows different modules to interact with only inhaled or exhaled air. The filters 24 and 26 filter out particulates or other materials from air prior to inhalation and also prior to air exiting the facemask. These filters can, for example, prevent a wearer from inhaling airborne pathogens and also prevents a wearer from disseminating airborne pathogens.

Figure 2:
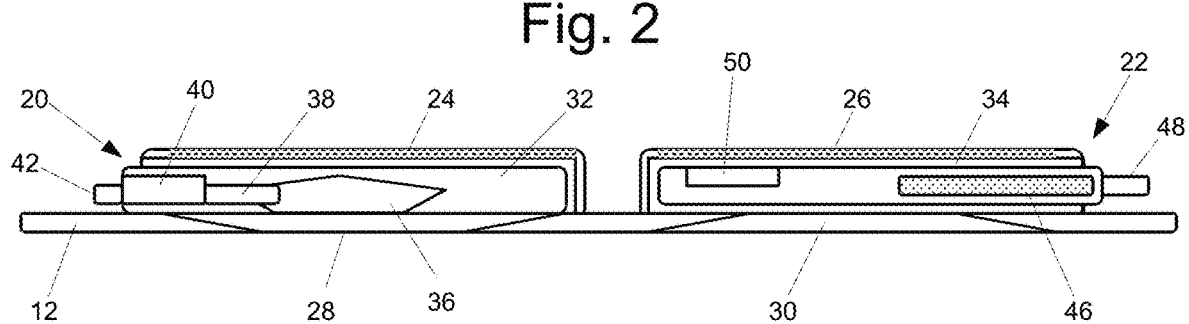
FIG. 2 is a cross-sectional view of the facemask having integrated modules in accordance with principles of the invention.

A wide variety of modules may be used with the facemask 10 in accordance with principles of the invention. FIG. 2 shows two exemplary modules 32 and 34. Module 32 is located in the exhaling socket 20 and includes a pressure sensor 36 or for detecting the force and volume of the exhaled air. Optionally, the pressure sensor 36 can be incorporated into the check valve. The pressure sensor 36 is connected to a microcontroller 38 powered by a battery 40 and having a USB port 42. The microcontroller 38 optionally includes wireless communication functionality. The module 32 can record and store information regarding the force and volume of air exhaled by a wearer over time. This information may then be downloaded via the USB port 42. Optionally, the USB port 42 may be used primarily to recharge the battery 40 while data regarding the wearer's force and volume of exhaled hair over time may be transmitted by the microcontroller 38 in real time to an app on a smart phone, tablet or other electronic device. The module 32 may also include a thermometer to detect the temperature of exhaled air, from which the wearer's body temperature may be deduced.

Inhalation module 34 is located in the inhaling socket 22 and includes a reservoir 46 containing a solution of vitamins and/or nutritional supplements. When the wearer inhales, he or she may depress the actuating button 48 which causes an atomizer or nebulizer to spray the solution in the reservoir as the wearer inhales. The aerosolized solution is then inhaled by the wearer. Those skilled in the art will appreciate that such a nebulizer may be utilized to administer a wide variety of vitamins, nutritional supplements, medicaments and other chemical compositions or substances to the wearer. The module 34 may optionally be programmed to eject a pre-determined amount of aerosolized solution at various time intervals. The module 34 may also optionally include a microcontroller 50 in wireless communication with a computer network, mobile network, or a software application on a smart phone, tablet or other electronic device. The microcontroller 50 may regulate the frequency and amount of aerosolized solution administered to the wearer, instead of or in addition to actuation by the button 48. The wearer may utilize the app to adjust the frequency and amount of solution administered. Optionally, the software application may be configured to automatically adjust the frequency and amounts of solution administered based on readings received from the exhalation module 32.

Figure 3:
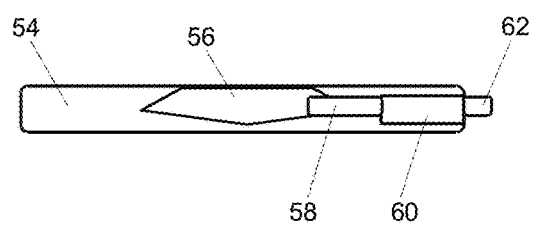
FIG. 3 is an alternative embodiment of a module for use with the facemask having integrated modules in accordance with the principles of the invention.

FIG. 3 shows an alternative inhalation module 54 similar to the exhalation module 32 and including a sensor 56 in communication with a microcontroller 58 powered by a battery 60 and having a USB port 62 for charging the battery and/or downloading information recorded regarding the force and volume of inhaled air over time. The inhalation module 54 may be used in conjunction with the exhalation module 32 to more accurately measure the wearer's cardiovascular activity. The exhalation module 32 and inhalation module 54 may also be used in conjunction to calibrate one or the other of these modules to compensate for air passing around the periphery of the mask rather than directly through the sockets 20 and 22.

Figure 4:
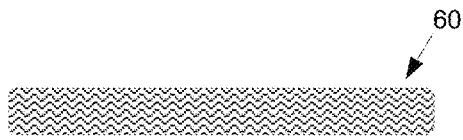
FIG. 4 is another alternative embodiment of a module for use with the facemask having integrated modules in accordance with principles of the invention.

FIG. 4 shows another alternative module 60 comprising simply an air filter. The filtration module 60 may be placed in either or both sockets 20 and 22 to further inhibit transmission of particulates through the facemask 10. This may be desirable, for example, when a wearer is known to be infected with an airborne pathogen. He or she may insert the filtration module 60 into the exhalation socket 20 provide added protection to persons in his or her vicinity. Similarly, if the wearer is in an environment where infection by an airborne pathogen is more likely, he or she may insert the filtration module 60 into the inhalation socket 22 for added protection.

Figure 5:
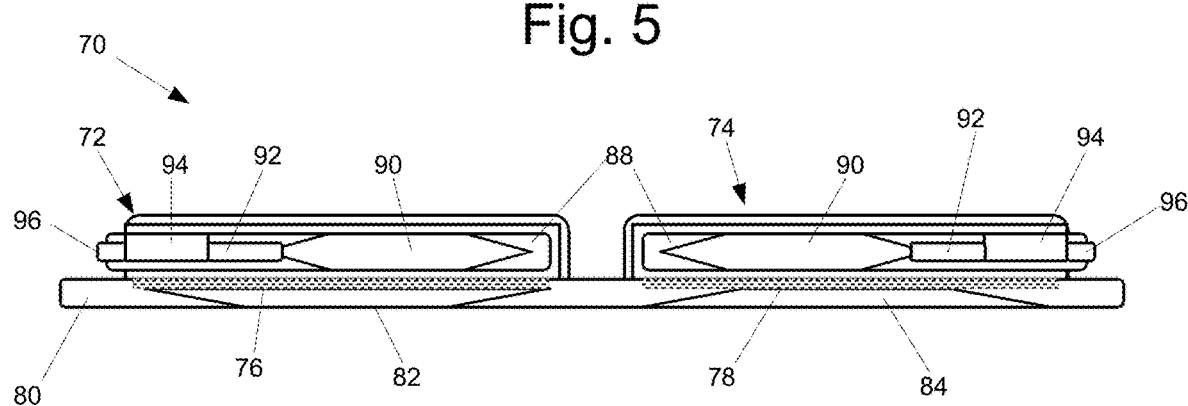
FIG. 5 is a cross-sectional view of an alternative embodiment of a panel of a facemask having integrated modules accordance with principles of the invention.

FIG. 5 shows an alternative embodiment of a facemask 70 having an exhalation socket 72 and an inhalation socket 74. In this embodiment, exhalation filter 76 and inhalation filter 78 are located within the panel 80 of the facemask, between the socket 72 and 74 and the check valves 82 and 84, respectively. Modules placed within the socket 72 and 74 will therefore monitor inhaled air prior to it being filtered and exhaled air after passing through the filter. FIG. 5 shows a panel 70 of a facemask where sockets 72 and 74 both hold modules for detecting substances in the air. Each module 88 includes a sensor 90, a microcontroller 92, a battery 94 and a USB port 96. The modules 88 may be configured to detect the same substance or different substances in the air. Optionally, the sensors 90 may each be capable of detecting multiple different substances and the microcontrollers 92 may selectively detect and record or transmit data regarding the amount of particular substances identified by each module 88. For example, the module 88 in the exhalation socket 72 may be used to detect the presence of a pathogen the wearer is known to carry. The module 88 may then be used to determine the efficacy of the exhalation filter 76 and removing the pathogen. The module 88 in the inhalation socket 74 may be used to detect a known pathogen the wearer wishes to avoid. If the pathogen is detected by the module 88 in the inhalation socket 74, it may alert the wearer to the presence of the pathogen so that the wearer may take additional precautions.

The modules 88 may be configured to identify any number of substances. As another example, both modules 88 may be configured to detect the amount of carbon dioxide and/or oxygen in order for the wearer to determine the efficiency of his or her respiration. The sockets shown in FIGS. 2 and 5 illustrate the different possible placements of filters around the sockets in the facemask. They are not intended to be alternative examples. That is, the sockets may include filters in the facemask panel itself, on the top of the socket, in both positions, and alternating positions, or a facemask may even include no filtration at all, instead relying on filters with in the modules themselves. The sensors may also be used to detect other substances. For example, the sensor module 88 in the exhalation socket 72 may be configured to determine blood alcohol content and alert the wearer when he or she is beyond the legal limit for driving. The sensor module 88 in the exhalation socket 72 may also be used to detect the presence of pathogens and alert the wearer that he or she has been infected. The sensor module 88 in the exhalation socket 72 may also be used to detect substances that indicate excessive physical exertion, lower high blood sugar, or markers indicating the possibility of cancer, diabetes, asthma, heart disease and other conditions. The module 88 may even be used to detect excessive belching.

The sensor module 88 in the inhalation socket 74 may similarly be used to detect a wide array of substances. For example, the sensor module 88 may be configured to detect carcinogens, asbestos, various pathogens, carbon monoxide, and other undesirable substances. The present invention may also be used by the military to detect nerve agents or other biological weapons and/or excessive radiation or radioactive substances. For example, a module may have a sensor similar to sensors found in commonly used radiation badges that allow the wearer to measure the amount of radiation he or she is exposed to.

Figure 6:
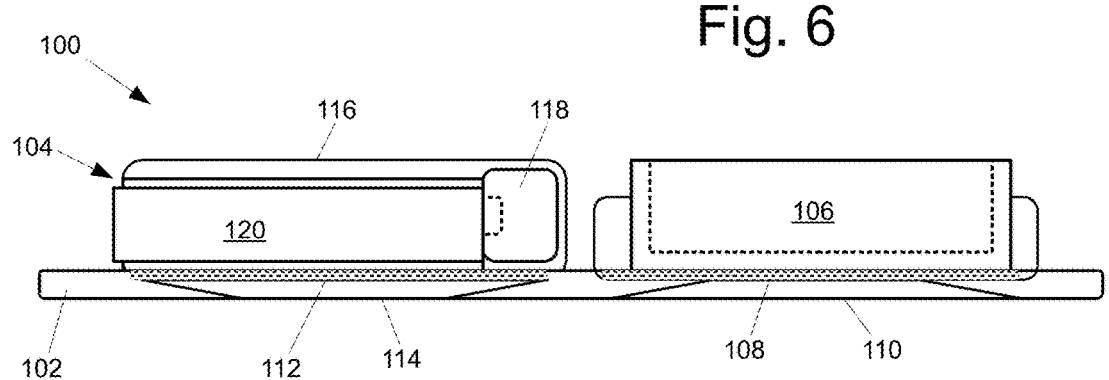
FIG. 6 is a cross-sectional view of another alternative embodiment of a panel of a facemask having integrated modules accordance with principles of the invention.

FIG. 6 shows another alternative embodiment of a mask 100. As with the other Figures, the dimensions are not to scale and have been exaggerated in some directions to more clearly depict the principles of the invention. The panel 102 of the mask 100 includes an exhalation socket 104 and an inhalation socket 106. The inhalation socket is positioned over a filter 108 and a check valve 110 which allows air to pass from outside the mask two inside the mask where it may be inhaled. The socket 106 is configured to retain a removable cartridge. The exhalation socket 104 is positioned over a section of the panel 102 that includes a filter 112 and a check valve 114 configured in a direction opposite to that of the check valve 110. The exhalation socket 104 is formed by a flap of material 116 extending over the panel 102 and containing a microcontroller 118. A module 120 is inserted into the socket 104 and plugged into a socket and a microcontroller 118. The microcontroller 118 then provides wireless communication with a software application as described above. The module 120 may be used in any manner as described above regarding different types of modules within the exhalation socket.

Figure 7:
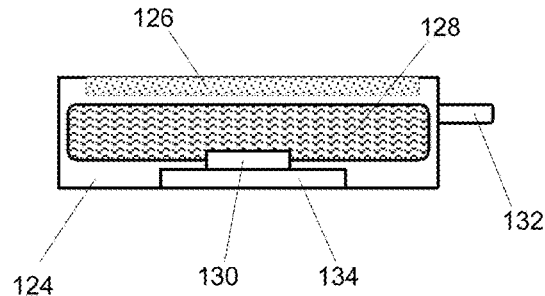
FIG. 7 is a cross-sectional view of another alternative embodiment of a module for use with a facemask having integrated modules in accordance with principles of the invention.

The socket 106 is configured to allow removable insertion of a variety of different types of cartridges configured to administer substances to the wearer of the mask. It may include tabs that allow a cartridge to snap in the place and may optionally include other mechanisms for removably securing a cartridge within the socket 106. FIG. 7 shows one example of a cartridge 124 that may be removably attached into the socket 106. The cartridge 124 is a vaporizer configured for use with a mask in accordance with principles of the invention. The cartridge 124 includes a filter 126, a reservoir 128 of vaping liquid, an atomizer 130, and actuating button 132 and an outlet 134. When the actuating button 132 is depressed, the vaping liquid is fed into the atomizer 130 which converts the vaping liquid into a vapor which then exits through the outlet 134 and may be inhaled by the wearer. The cartridge 124 may be powered by rechargeable battery, not shown. The reservoir 128 may be refilled as desired.

Figure 8:
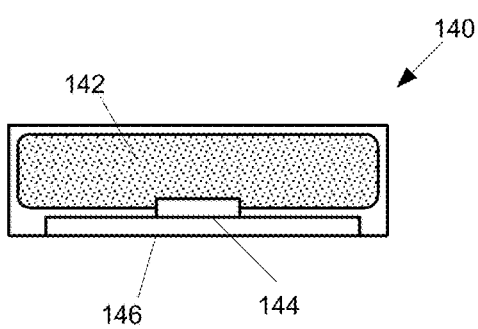
FIG. 8 is a cross-sectional view of another alternative embodiment of a module for use with a facemask having integrated modules in accordance with principles of the invention.

FIG. 8 shows an alternative embodiment of a cartridge 140 which also acts as a vaporizer. It includes a reservoir 142, an atomizer 144, and an outlet 146. The cartridge 140 is actuated by air pressure caused by the wearer inhaling. When the wearer inhales, the pressure changes detected by the cartridge 140 which then actuates the atomizer 144, thus producing a vapor which is inhaled by the wearer. In addition to being used as a purely recreational device, the cartridge 140 may also be used to nebulizer solutions of vitamins, medicaments or other substances for the benefit of the wearer.

Figure 9:
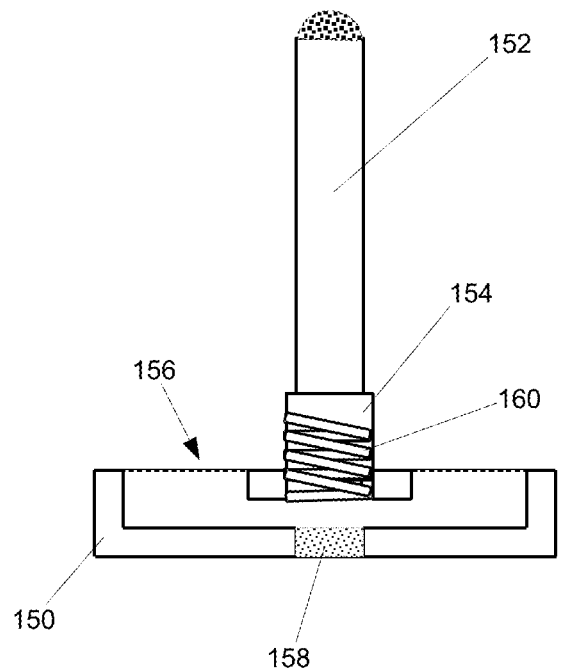
FIG. 9 is a cross-sectional view of another alternative embodiment of a module in an extended configuration for use with a facemask having integrated modules in accordance with the principles of the invention.
Figure 10:
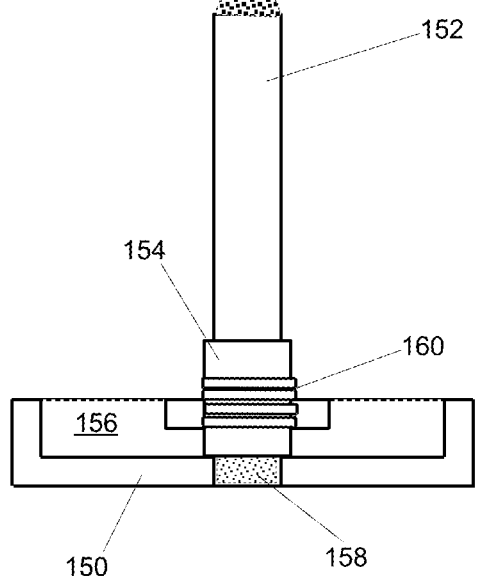
FIG. 10 is a cross-sectional view of another alternative embodiment of a module in a depressed configuration for use with a facemask having integrated modules in accordance with principles of the invention.
Figure 11:
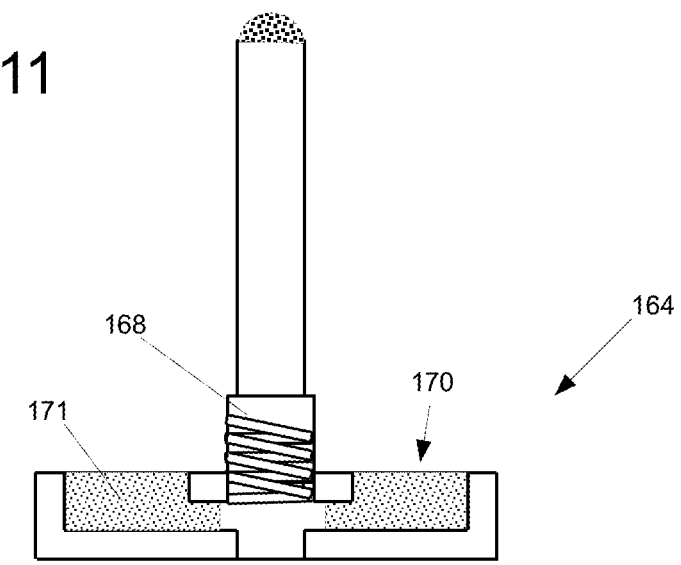
FIG. 11 is a cross-sectional view of another alternative embodiment of a module for a facemask having integrated modules accordance with principles of the invention.

FIGS. 9 and 10 show another alternative embodiment of a cartridge 150 which may be used with the socket 106. Cartridge 150 may be used with an electronic cigarette or a regular cigarette. A cigarette 152 is placed within the cigarette holder 154 which is surrounded by an air inlet 156. A filter 158 is positioned directly below the cigarette holder 154 and provides a passage to the bottom of the socket 106 and its associated check valve. The cigarette holder 154 is biased by a spring 160 which holds the cigarette away from the filter 158 so that air flows through the air inlet and into the filter 158. When desired, the wearer presses downward on the cigarette holder 154 such that it abuts the filter 158. When the wearer inhales, air is drawn through the cigarette instead of the air inlet 156. The wearer then releases the cigarette and the spring 160 returns it to an extended position such that air may flow through the air inlet and into the filter 158. This allows a wearer to smoke without removing his or her mask. FIG. 11 shows an alternative embodiment of a cartridge 164 which includes a spring biased cigarette holder 168 and an air inlet 170. In cartridge 164, an air filter 171 is provided which extends throughout the entire air inlet 170.

Figure 12:
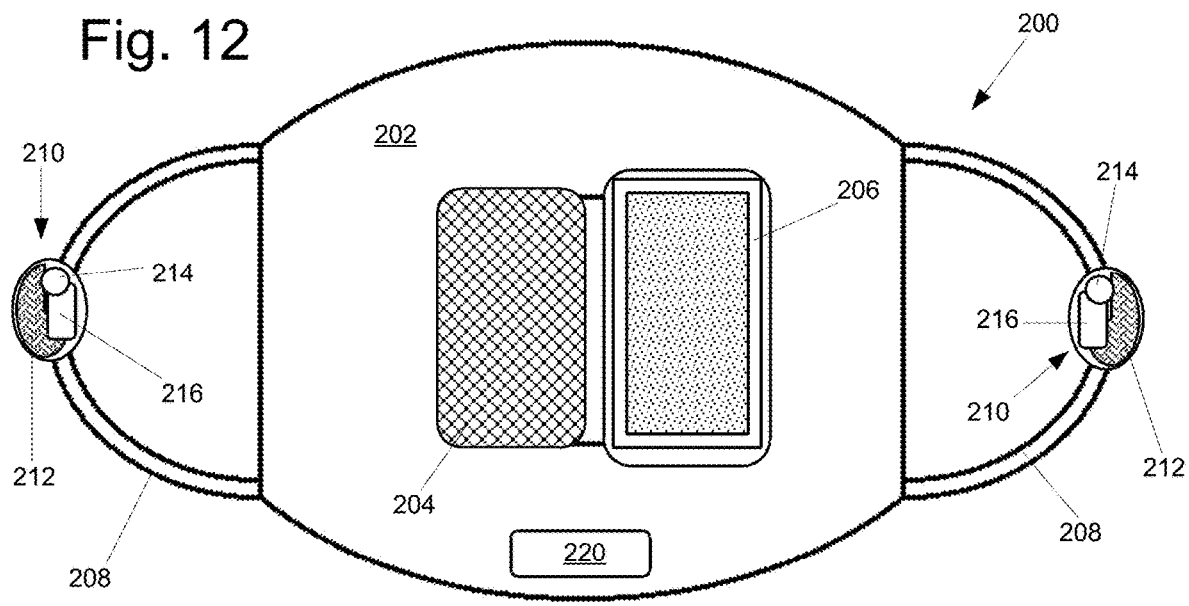
FIG. 12 is an outside view an alternative embodiment of a facemask having integrated modules accordance with principles of the invention.

FIG. 12 shows another alternative embodiment of a facemask 200 having a panel 202 with two sockets 204 and 206. The facemask 200 includes two opposing elastic bands 208 for securing the facemask to a wearer's ears and the panel across the wearer's mouth and nose. Facemask 200 also includes two receptor pads 210. Each receptor pad 210 includes an absorbent patch 212, a thermometer 214 and a sensor 216. The sensor 216 may be configured to detect a variety of chemicals. In this embodiment, the pads are positioned such that they are located behind and/or above the ears which may be preferred to expose the pads two sweat from the wearer's head. Thermometers 214 monitor the wearer's temperature. This information is sent to a microprocessor 220 which is in communication with both receptor pads 210. The absorbent patches 212 absorb sweat from the wearer. These sensors 216 measure the amount of sweat absorbed by the patches 212 and also detect various substances in the wearer's sweat. The components of the wearer's sweat may indicate the wearer's blood sugar level, and the pH of the sweat may also be measured and provided to the microprocessor 220. Pads 210 are intended to be exemplary. In this embodiment, they are oval and located on the bands 208 such that they would be placed behind the wearer's ears. The pads 210 may optionally have other shapes and be located elsewhere on the facemask 200. There may be only one patch 210 or there may be a plurality of patches 210. In addition, the thermometers need not be adjacent to the absorbent patches and sensors. Optionally, the sensors may not be of the type that produce an electrical current or other signal in response to detecting chemical compositions. The sensor may simply be a pad that changes color over time, such as a litmus pad that indicates the pH of the wearer's sweat. The pads 210 may also optionally be placed at other locations along the elastic bands or optionally on the panel 202 of the facemask.

The microprocessor 220 is in wireless communication with a electronic device which has a software application that uses data from the sensors 216, the thermometers 214, as well as information from the modules in the socket 204 and socket 206 to evaluate the health of the wearer. The software application may also, in some instances, alert the wearer's doctor or another person when the wearer's health is in danger. For example, if a diabetic child is wearing the mask, the software application may alert the child's parents if the child's blood sugar changes to drastically. In this embodiment, the sockets 204 and 206 do not have integrated check valves and instead only provide filters. Modules placed with in the sockets have individual check valves themselves. This prevents a wearer from accidentally inserting the wrong modules into the wrong sockets. Because the modules, not the sockets provide the check valves, it does not matter which socket a modules placed in, so long is the module is inserted in the correct orientation.

Figure 13:
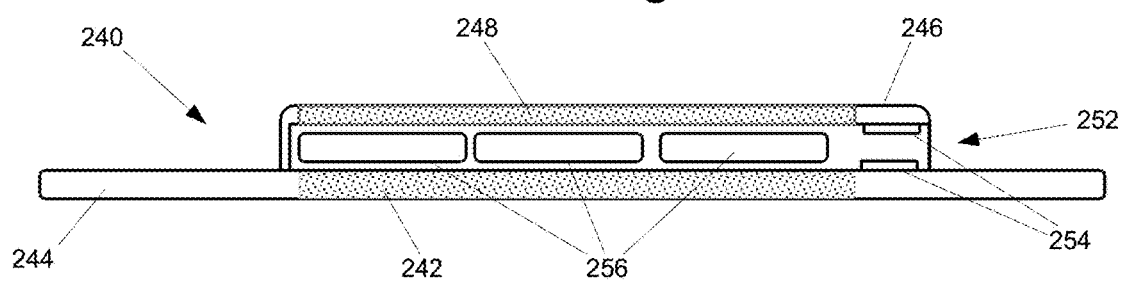
FIG. 13 is a cross-sectional view of a socket containing a plurality of modules for a facemask having integrated modules in accordance with principles of the invention.

FIG. 13 shows an alternative embodiment of a module socket 240 in accordance with principles of the invention. The socket 240 is positioned over a filter 242 incorporated into a panel 244 of a facemask. The socket is formed from a smaller panel 246 of the material extending over the panel 244 and also as an incorporated filter 248. The opening 252 the socket 240 has opposing complementary hook and loop panels 254 to securely close the socket 244 and retain the modules 256 within the socket 240. The socket 240 is larger than other sockets shown in previous exemplary embodiments, and is able to accommodate multiple modules 256 in parallel or stacked on top of each other. The modules may be inhalation modules, exhalation modules or combinations thereof. The modules 256 have their own check valves so that it is unnecessary to include one-way valves in the socket 240. The sockets 204 and 206 are similar to module socket 240, but do not include a closing mechanism such as hook and loop panels. Optionally, the facemask 200 may be modified to include one or more module sockets 240 shown in FIG. 13.

Figure 14:
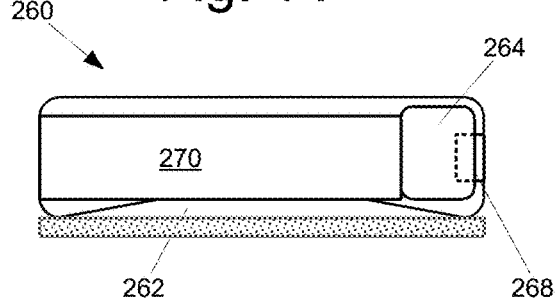
FIG. 14 is a cross-sectional view of an alternative embodiment of a module for use with a facemask having integrated modules accordance with principles of the invention.

FIG. 14 shows an exemplary inhalation module 260 in accordance with principles of the invention. The inhalation module 260 includes a check valve 262 that actuates when the wearer of a mask inhales. The module 260 also includes a microcontroller 264 with a USB port 268. The inhalation module 260 also includes a chamber 270 into which any of a variety of sensors or substance dispensers, as explained above, may be inserted and connected to the microcontroller 264. For example, the chamber 270 may accommodate a sensor to detect the presence of pathogens or toxic substances in the ambient air.

Figure 15:
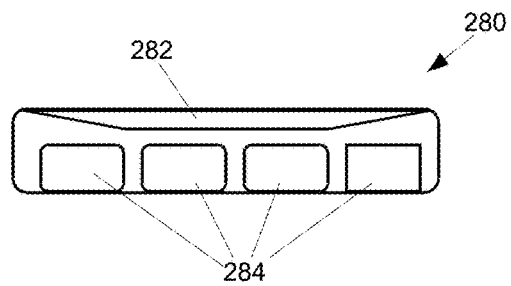
FIG. 15 is a cross-sectional view of another alternative embodiment of a module for use with a facemask having integrated modules accordance with principles of the invention.

FIG. 15 shows an exemplary exhalation module 280 in accordance with principles of the invention. Exhalation module 280 includes a check valve 282 positioned behind a battery of sensors 284. The check valve prevents outside air from affecting the readings of the sensors 284 so that they only detect the presence of various substances from air exhaled from the wearer. These sensors may be configured to detect a variety of measurements, such as pH, the presence of pathogens, blood alcohol level, blood sugar level, markers for cancer or other diseases, and the like. The sensors 284 may be passive sensors. That is, instead of being powered in taking electrical or mechanical readings, they react chemically. For example, a pH sensor may change color over time according to the pH of the exhaled air. After a predetermined amount of time, the wearer may visually check the sensors in the same way the chemistry of a swimming pool may be measured by checking a test strip.

Figure 16:
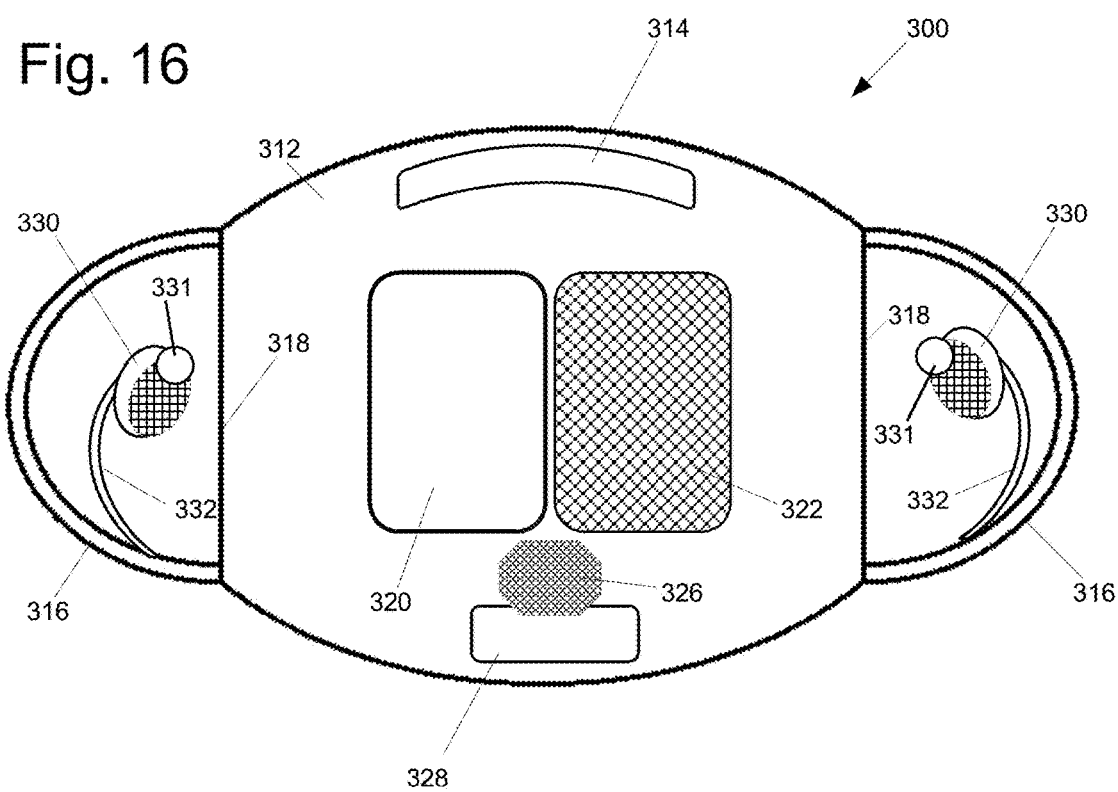
FIG. 16 is an inside view of another alternative embodiment of a facemask having integrated modules in accordance with principles of the invention.

FIG. 16 shows the inside of another alternative embodiment of a facemask 300 having integrated modules in accordance with the principles of the invention. Like the other embodiments, facemask 300 includes a panel 312 configured to fit over the mouth and nose of a wearer. The facemask 300 is held in place by two elastic bands 316 on each of its lateral sides 318 that extend about the wearer's ears. A rigid or semirigid supports 314 may be adjusted to more comfortably fits a wearer. Facemask 300 also includes two sockets 320 and 322 for accommodating inhalation and/or exhalation module. In addition, facemask 300 includes a microcontroller 328 that provides wireless communication, such as for example via Bluetooth®, to a smart phone or other electronic device. A microphone 326 is positioned inside the mask proximal to the wearer's mouth and is connected to the microcontroller 328. The facemask 300 also includes two earpieces 330 on each of its lateral sides 318 and connected to the microcontroller 328 by wires 332. In this embodiment, the wires 332 extends from the elastic bands 316. Optionally, the earpieces 330 may themselves be connected via Bluetooth® or by wires extending to or from different regions of the facemask 300. The inclusion of a microphone 326 and earpieces 330 into the smart inhalation mask allows the facemask 300 to operate as a cell phone. This is more convenient than using a cell phone while wearing a mask and also produces better sound quality through the microphone 326. As with the other facemasks described above, the panel 312 of the facemask 300 may be comprised of any material, including a semi permeable material such as cotton or wool, or an air impermeable material such as leather, carbon fiber, plastic or the like. The use of an air impermeable material concentrates airflow through the inhalation and exhalation sockets 320 and 322. The earpieces 330 also include thermometers 331 which may be used to measure the wearer's temperature.

Figure 17:
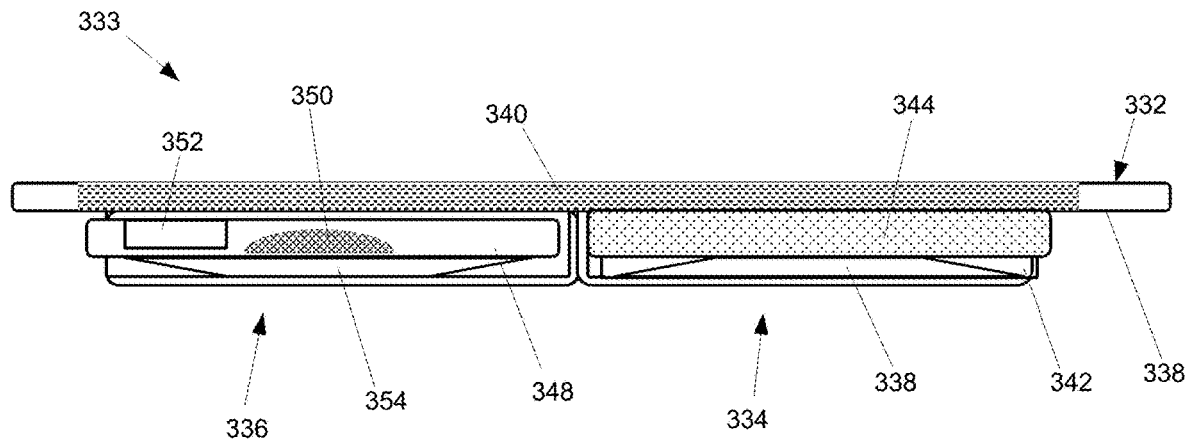
FIG. 17 is a cross-sectional view of another alternative embodiment of a panel for a facemask having integrated modules in accordance with the principles of the invention.

FIG. 17 shows another alternative embodiment of a facemask 333 having a panel 332. In this embodiment, the inhalation socket 334 and exhalation socket 336 are located on the interior side 338 of the panel 332. A filter 340 is integrated into the panel 332 and is substantially coextensive with the inhalation and exhalation sockets 334 and 336. It may be desirable to include the sockets 334 and 336 on the inside of the mask to prevent damage and/or snagging of the sockets on external objects. It also provides direct access to modules within the sockets from the inside of the mask. Here, the inhalation socket 334 includes a module 342 that includes an additional filter 344 and a check valve 338 that only allows airflow from the outside to the inside of the mask panel 332. Module 348 located in the exhalation socket 336 includes a microphone 350 and a microcontroller 352 providing wireless communication, such as for example via Bluetooth®, to an electronic device. Module 348 allows a facemask 333 to operate as a cell phone or similar communication device even though the panel 332 itself is not equipped with a microphone. Thus, any facemask having a socket may be converted into a communication device. In this embodiment, the microphone 350 is positioned behind the check valve 354. Optionally, the microphone may be positioned in front of or next to the check valve 354. The module 348 may also optionally include additional sensor words or other devices as explained above.

Unless explicitly stated otherwise, the various features of the exemplary facemasks may be combined in ways not explicitly shown in the drawings unless explicitly stated otherwise or the features are clearly mutually exclusive. For example, the module 348 in FIG. 17 may be incorporated into a socket such as the one shown in FIG. 13. Similarly, the sockets shown in FIG. 13 may be integrated into any of the facemask panels shown in any of the Figures. In addition, the microcontrollers provided herein may perform additional functions for which microcontrollers are commonly employed unless clearly excluded explicitly or by the context of the foregoing descriptions. For example, the microcontroller 328 of FIG. 16 may also be used to store audio files, such as music playlists, which may be played through the earpieces 330. The same holds true for the features described in the additional alternative embodiments described below.

When the facemask itself and/or one or more of its modules are in communication with a electronic device, it may be used in many different ways. For example, it may be in communication with the Internet and platforms on the internet. The software application and connected platforms may be configured to automatically take action when certain biometric data is detected by the facemask and/or modules. For example, when the software application, based on data obtained by the facemask and/or modules, detects that the wearer has exerted a predetermined amount and/or type of energy, the application or platform may interpret this as performance on a contract such as a smart contract. The Wearer may then be rewarded monetarily by transferring money into a bank account or by being transferred a cryptocurrency recorded on a distributed block chain ledger. Optionally, when the wearer reaches a predetermined goal that fact may be automatically posted on one or more social networking or other platforms. Similarly, the physiological data obtained by the facemask and or integrated modules may also send information to an insurance company platform, which may then raise or lower insurance premiums for the wearer. For example, if a module the facemask detects that the wearer's blood alcohol level is above a predetermined amount, the microcontroller detects that it is within Bluetooth range of the wearer's automobile, and a GPS chip detects that the wearer is moving at a philosophy only achievable with the automobile, this information may be sent to an insurance company, to the wearer's spouse or parents, or even to law enforcement. Similarly, when a module detects that the wearer has contracted a communicable disease, for example COVID, a GPS chip may be actuated to record the movements of the wearer to assist in contact tracing.

Figure 18:
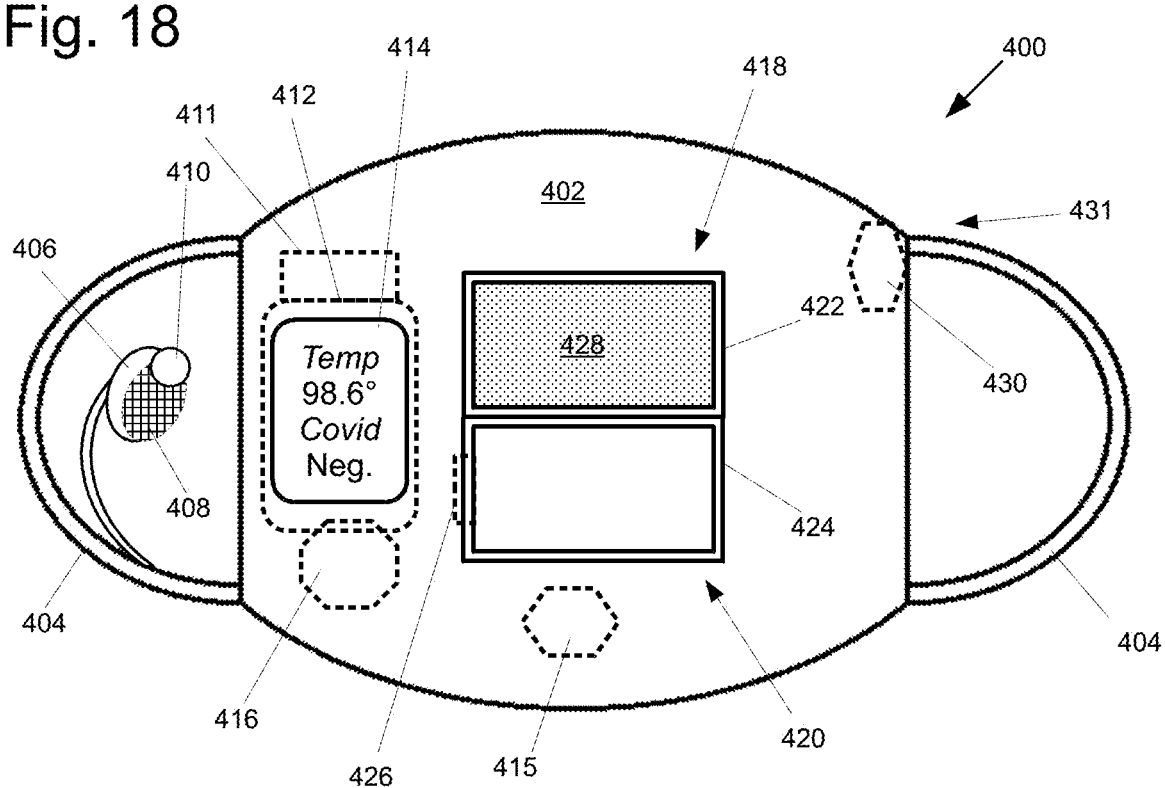
FIG. 18 is an inside view of another alternative embodiment of a facemask having integrated modules in accordance principles of the invention.

FIG. 18 shows another alternative embodiment of a facemask 400 having integrated modules. Facemask 400 is formed from a panel 402 having two lateral elastic bands 404. An earpiece 406 including a speaker 408 and a thermometer 410 is located on one side of the facemask 400. In addition, facemask 400 includes a heart rate monitor located at an upper corner 431. Heart rate monitor 430 may be of the type that measures light reflected through the skin and thus perform better when held against the wearer's skin. Because the upper corner 431 is adjacent to one of the bands holding the panel 402 to the wearer's face, it will almost always be in direct contact with the wearer's skin, making this location a good point to place a heart rate monitor 430. Optionally, to earpieces 406 may be included as shown in FIG. 16. Facemask 400 includes a microcontroller 412 connected to a video screen 414, a battery 411, a microphone 415, and a GPS chip 416 which allows the microcontroller 412 to determine the approximate location of the facemask 400. Facemask 400 includes an upper socket 418 and a lower socket 420 configured to receive complementary modules. Previous embodiments shown above described facemask having sockets which take the form of a more typical socket. In this embodiment, the sockets are configured to have a module snap into place. The sockets 418 and 420 have peripheral magnetic frames 422 and 424, respectively. The lower socket 420 includes a micro USB port 426 that provides communication between the module and the microcontroller 412. The microcontroller 412 may also optionally include a port or opening for accommodating a SIM card as well as additional functionality so that the facemask itself may act as a voice activated mobile phone.

Facemask 400 therefore has substantially expanded functionality over not only typical facemasks but also many different types of "smart" wearable technology. Facemask 400 is a mobile phone, and also includes the functionality found on wrist worn "smart" devices such as a FitBit® or Apple iWatch®. It can measure heart rate, both at rest and during exercise, and can also measure breathing rate, lung capacity and, when the correct modules are incorporated into it, the facemask 400 also detects the level of carbon dioxide in exhaled breath as well as the presence or absence of a variety of other chemicals. This is true even for chemicals found in very small quantities in exhaled breath because substantially all of the exhaled breath will flow over and exhalation module, allowing it to collect and detect substances over a long period of time and thus in quantities sufficient to be quantified by a sensor.

In addition to displaying this information on the mask, the microcontroller 412 may store or wirelessly transmit physiological information regarding the wearer of the facemask 400 to an electronic device or wireless network. This may be done in real time. The results may be provided over a wireless network or otherwise to wearer's physician, personal trainer, family members, insurance company or any other entity the wearer wishes to share the information with. The microcontroller may also use various cryptographic or other protocols to limit dissemination of this information in accordance with HIPAA or other laws. If the wearer is injured, for example in an accident, or suffering a stroke, the data recorded by the facemask 400 may be provided to emergency medical technicians and thus decrease the amount of time required to analyze the status of an injured person in an emergency room or by emergency medical personnel. The microcontroller 412 may thus optionally include a USB port for allowing a medical device to attached to it and download information regarding the wearer. Optionally, this information may be displayed on the video screen 414 of the mask itself. The video screen 414 may be used to display the wearer's current temperature, heart rate, pulse, blood oxygen level (determined by amount of carbon dioxide in exhaled breath) as well as averages for each of those metrics over a given period of time.

FIG. 18 shows a module 428 comprising simply a filter in the upper socket 418. The module 428 includes a check valve, not shown, which only permits airflow in an inward direction, as described in previous examples of check valves. A ferromagnetic band extends around the periphery of the module 428 and engages the magnetic frame 422 of the socket 418, thereby securing the module 428 in the socket 418. Those skilled in the art will appreciate that other materials may be suitable to provide releasable attachment of a module to a socket. For example, complementary strips of a hook and loop fastener may be used. Alternatively, a tongue and groove type fastener may be used. Optionally, the module 428 may be comprised of only a filter without a check valve. A wearer could insert two modules comprised only of a filter surrounded by a ferromagnetic band if the wearer only desires to filter air flowing in and out of the mask. In this embodiment, neither of the two sockets 418 and 420 is designated as an inhalation socket or an exhalation socket. Which socket or sockets inhaled and/or exhaled air passes through depends upon the components of the module, not the socket or the panel of the facemask 400.

Figure 19:
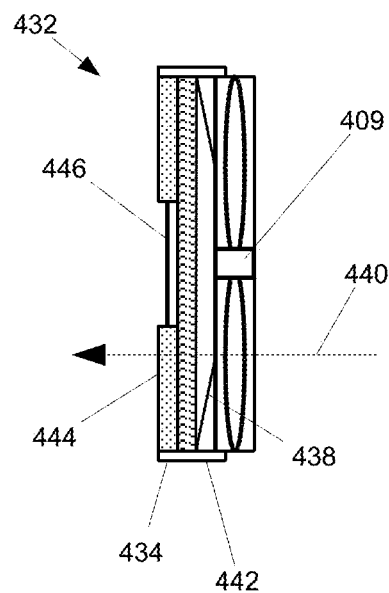
FIG. 19 is a cross-sectional view of another alternative embodiment of a module for a facemask having integrated modules in accordance with principles of the invention.
Figure 20:
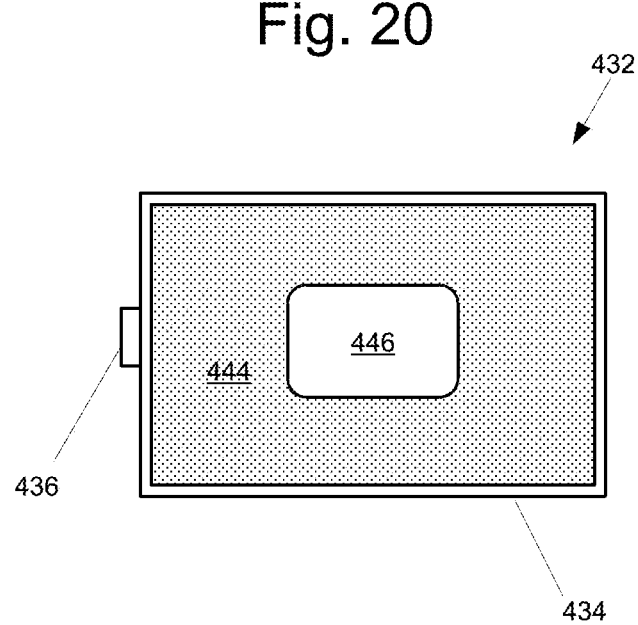
FIG. 20 is a front view of another alternative embodiment of a module for a facemask having integrated modules accordance with principles of the invention.

A module 432, shown in FIGS. 19 and 20, has a magnetic band 434 extending around its periphery which engages the magnetic frame 424 of the socket 420, thereby providing removable and substantially airtight attachment to the facemask 400. A USB connector 436 attaches to the USB port 426. The module 432 includes a check valve 438 that only permits airflow in an outward direction as indicated by arrow 440. A middle layer 442 is comprised of an air permeable material that includes material that changes color when exposed to a communicable disease. The outside layer 444 has a filter that prevents undesirable particles from exiting outside the mask and also includes a central window 446 of an airtight transparent material such as glass or clear plastic. If the wearer has the communicable disease, for example COVID, then the middle layer 442 changes color and this color change will be visible from the outside. Thus, persons within the vicinity of the wearer will be alerted to the fact that the wearer is the carrier of the communicable disease.

In this embodiment, the module 432 also generates an electrical signal when a communicable disease is detected. The signal travels via the USB port 436 to the microcontroller which can display the status of a wearer on the video screen 414. FIG. 18 shows a message on the video screen 414 indicating that the wearer is COVID negative. The video screen 414 of this embodiment also displays the wearer's temperature as measured by the thermometer 410. The wearer may issue a voice command which is received by the microphone 415 instructing the video screen 414 to display the wearer's current body temperature and whether the wearer has contracted a communicable disease. This may be beneficial for checking the status of passengers prior to boarding airplane, a train or other transportation. Optionally, the microcontroller may detect a specific predetermined signal generated by an electronic device at a ticketing desk which automatically displays this information prior to allowing the wearer to purchase a ticket for an airplane, bus, train or other transportation. Those skilled in the art will appreciate that it often will be unnecessary for the module 432 two include both the central window 446 and the USB port 436 for sending an electronic signal. These features are redundant and a module may include only one or the other, not both features. Those skilled in the art will also appreciate that the middle layer 442 may be configured to change color based on various other conditions. For example, the color may change if the wearer's blood alcohol level has exceeded a predetermined amount, or based on a variety of other factors.

Module 432 also includes a micro turbine 409 that is actuated whenever the wearer exhales. For clarity and simplicity, the turbine 409 is shown as simply a fan. Those skilled in the art will appreciate that there are a variety of small thin devices capable of harnessing energy from fluidflow, such as airflow, some of which are not even technically a turbine, which would also be suitable. Here, for simplicity, the term "turbine" is used generally to refer to any device capable of generating electricity from airflow. The energy generated by the turbine 409 may be stored by the battery 411. Those skilled in the art will appreciate that this device may be incorporated into any of the modules shown or described herein unless explicitly stated otherwise or it is clear from the context. Typically, such a device is incapable of generating sufficient electricity to operate anything except for the smallest, lowest power devices. However, because it is constantly operating over a long period of time continuously, it will continue to generate electricity while the other components of the facemask are mostly inactive. This allows generated electricity to accumulate over time and be stored in the battery. By generating its own electricity, a facemask in accordance with principles of the invention may supply power to a microcontroller or any modules requiring electric current to perform properly, indefinitely.

Figure 21:
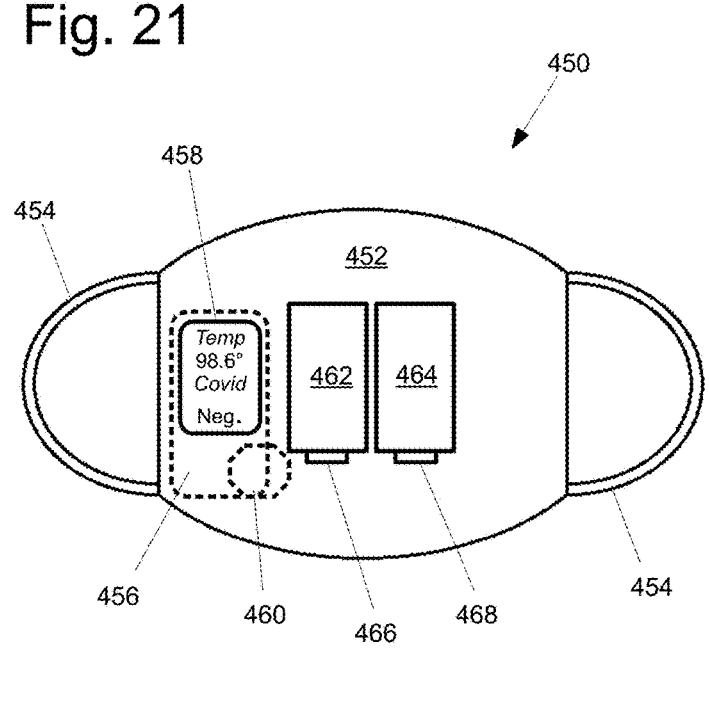
FIG. 21 is an inside view of another alternative embodiment of a facemask having integrated modules in accordance principles of the invention.

FIG. 21 shows another alternative embodiment of a facemask 450 having integrated modules in accordance with the principles of the invention. Facemask 450 is formed from a panel 452 having two lateral elastic bands 454 for securing the panel 452 over the mouth and nose of a wearer. In this embodiment, a microcontroller 456, a video screen 458, and a GPS chip 460 are all integrated into the panel. The facemask 450 includes a left socket 462 and a right socket 464 arranged side-by-side, and have electronic connection ports 466 and 468, respectively, at their lower end to allow modules within the sockets to communicate with the microcontroller 456. The microcontroller 456 preferably has wireless communication capabilities to connect with a nearby electronic device or computer network. Facemask 450 is similar to the facemask 400 shown in FIG. 8 in that it allows the facemask itself to display information about the wearer on the video screen 458. It may also optionally include a microphone and/or earpieces as described above for facemask 400.

Figure 22:
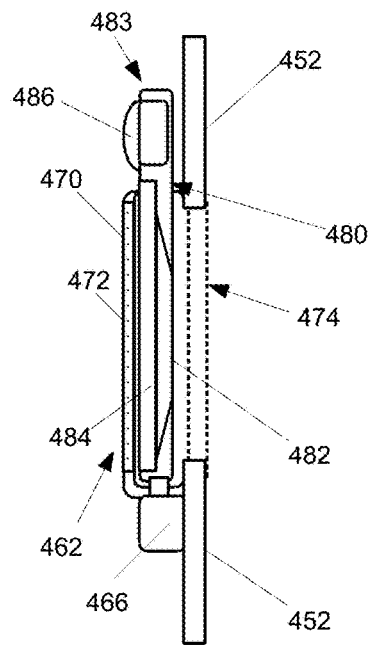
FIG. 22 is a cross-sectional view of another alternative embodiment of a module attached to a socket for use with a facemask having integrated modules in accordance with principles of the invention.

FIG. 22 shows another alternative embodiment of a module 480 incorporated into the left socket 462 of the facemask 450. Module 480 may also be used with facemask 450 or in conjunction with other sockets shown and described in other exemplary facemasks above. The socket 462 is formed by a panel 470 with an integrated air filter 472. In this embodiment, the panel 470 is rigid. Optionally, a flexible fabric may be used to form panel 470 as described and other embodiments above. The opening 474 of the panel 452 is substantially coextensive with the rigid panel 470. Previously described embodiments of facemasks include regions of the facemask panel which are coextensive with a socket or sockets which contain a check valve, a filter or other structure. In this embodiment, the region of the panel 452 which is substantially coextensive with the socket 462 is simply an opening 474. Therefore the direction of airflow, any filtration, sensing or other functionalities must be contained within a module placed within the socket 462.

The module 480 is positioned inside the socket 462 and includes an external region 483 which extends out of the socket 462 so that it is clearly visible. A check valve 482 on the inner side of the module 480 which only permits airflow in the outward direction. The outer side of the module 480 includes a sensor 484 for detecting the presence of a chemical, microbe or other objects in the wearer's exhaled air. An indicator light 486 located in the external region 483 provides a visual signal indicating the status of the sensor. For example, if the sensor has had insufficient time to analyze the wearer's exhaled air, the indicator light 486 will blink. If the sensor 484 detects the substances it tests for, it will emit red light. If nothing is detected, the light will emit green light. Both the sensor 484 and the indicator light 486 may be supplied power through the connection port 466. Optionally, the module 480 may include multiple sensors, each with its own indicator light.

Figure 23:
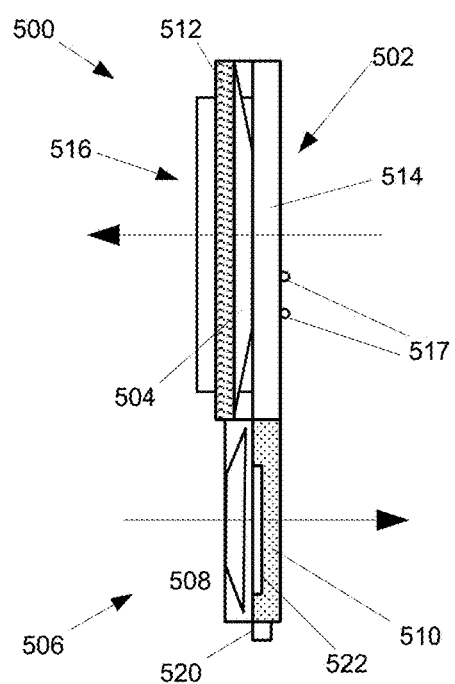
FIG. 23 is a cross-sectional view of another alternative embodiment of a module for use with a facemask having integrated modules in accordance with principles of the invention.
Figure 24:
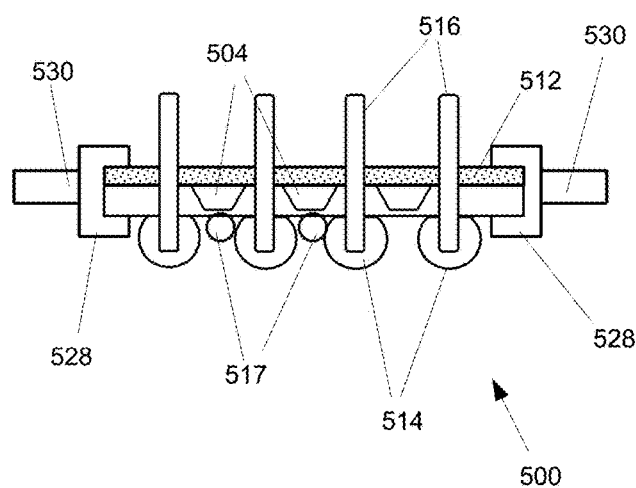
FIG. 24 is a cross-sectional view of another alternative embodiment of a module for use with a facemask having integrated modules in accordance with principles of the invention.

FIGS. 23 and 24 show an alternative module 500 in accordance with the principles of the invention. Module 500 includes an upper region 502 having one or more check valves 504 that allows air to flow in an outward direction, and a lower region 506 having a check valve 508 that allows air to flow in an inward direction. The lower region 506 also includes an air-permeable inner layer 510 of material that has an aerosolizable substance adsorbed to it. The upper region 502 includes an outer filter layer 512 that prevents objects such as communicable diseases from exiting the facemask. The inside surface of the upper region 502 has a smooth hydrophobic surface and includes a series of vertical, or longitudinal, smooth hydrophobic ribs 514 connected to a heatsink 515. In this embodiment, the heatsink 515 is formed by a plurality of fins 516 which extend partially into the hydrophobic ribs 514 and extend through the upper region 502 and protrude out of the outer filter layer 512. When the wearer exhales, his or her breath flows over the ribs 514 and liquid such as saliva suspended in the breath condenses on the ribs 514 which have been cooled by the heatsink 515. Because the inner surface and ribs 514 are hydrophobic, this liquid forms droplets 517 which then slide downward into the air permeable inner layer 510 of the lower region 506. The substance adsorbed to the inner layer 510 dissolves in the liquid and substance becomes aerosolized by air passing through the lower region 506 when the wearer inhales. The module 500 thus not only filters outgoing air to prevent the spread of the communicable disease, but also nebulizes and delivers a substance to the wearer.

In this embodiment, the heatsink 515 is a passive heatsink formed by a plurality of independent, unconnected heatsink fins 516, each one integrated into a separate rib 514. The heatsink fins 516 may optionally be interconnected and may also optionally have different configurations. For example, instead of each of the ribs 514 having a single heatsink fin 516 extending along its length, each rib 514 may have a plurality of in-line fins. Those skilled in the art will appreciate that there are a variety of suitable configurations for the heatsink 515. The heatsink may optionally be either passive or active. The module 500 may also optionally include a plug 520 to provide electrical communication through a port such as ports 466 and 468 of facemask 450. This may be used to send a signal to the microcontroller 456 that sufficient liquid has entered the air permeable region 510 so that the substance will be aerosolized. Optionally, the plug 520 may be used to supply electricity to a heater 522 to increase the rate at which the substance is aerosolized. The plug 520 may also optionally be used to provide a power to an active heatsink that is electrically powered.

FIG. 24 shows the module 500 in a socket 526 formed from two opposing U-shaped channels 528 that secure the module 500 in place within the socket 526. The module 500 is simply slid into the two opposing U-shaped channels 528 which are made from a rigid material and are connected to the panel 530 of a facemask.

The substance adsorbed to the air permeable region 510 may be a supplement, a medicine, a medicament, a breath freshener, or any other substance that may be aerosolized. Asthma relief medicines, mint breath fresheners, vaporizer flavors, nicotine, vitamins, herbal medicines, and nutritional supplements are non-exhaustive examples of substances that may be incorporated into the air permeable region 510.

Figure 25:
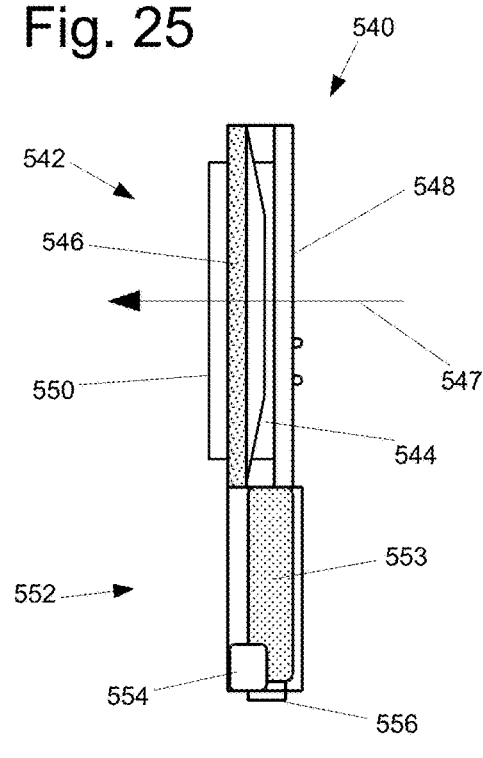
FIG. 25 is a cross-sectional view of another alternative embodiment of a module for use with a facemask having integrated modules in accordance with principles of the invention.

FIG. 25 shows another alternative embodiment of a module 540 in accordance with the principles of the invention and adapted to collect a saliva sample and detect substances within the sample. The module 540 includes an upper region 542 similar to the upper region 502 of module 500 described above. It includes a check valve 544 limiting airflow to an outer direction, an outer filter 546 and a plurality of smooth, vertical ribs 548. The vertical ribs 548 along with the entire inside surface of the upper region 542 have a hydrophobic coating and a plurality of heatsink fins 550 protruding from the outer filter 546. The lower region 552 of the module 540 differs from that of the module 500. The lower region 552 has a receptacle 553 for collecting saliva from the wearer's exhaled breath that condenses and drops down from the upper region 542. The lower region 552 may optionally include a sensor 554 for detecting a substance, such as a communicable disease, and a plug 556 for connecting to an electrical communication port to supply power to the sensor and/or to transmit a signal from the sensor 554 to a microcontroller in the facemask indicating whether or not a substance has been detected.

If the module 540 does not include a sensor 554 and a plug 556, it may serve only as a receptacle. After an adequate amount of saliva is collected in the receptacle, it may be removed and the saliva within it may be analyzed.

Figure 26:
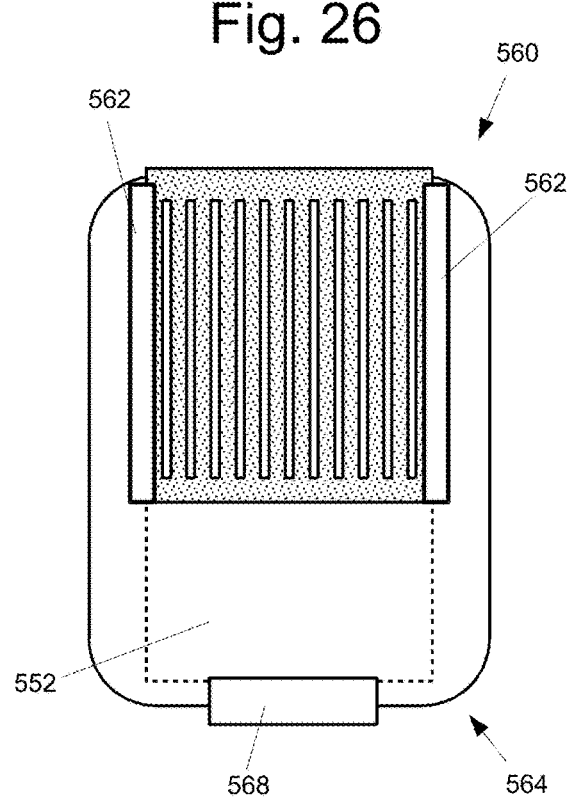
FIG. 26 is an outside view of another alternative embodiment of a module attached to a socket for use with a facemask having integrated modules in accordance with principles of the invention.

FIG. 26 shows another alternative embodiment of a socket 560 adapted for use with a module 540 in accordance with the principles of the invention. The socket 560 is formed from two opposing longitudinal U-shaped channels 562 formed from a rigid material. To insert the module 540 into the socket 560, the module 540 is slid downward through the tops of the U-shaped channels 562. The socket 560 includes a lower, air impermeable socket region 564 for housing the lower region 552 of the module 540, and includes a port 568 for providing electrical communication to the module 540.

Figure 27:
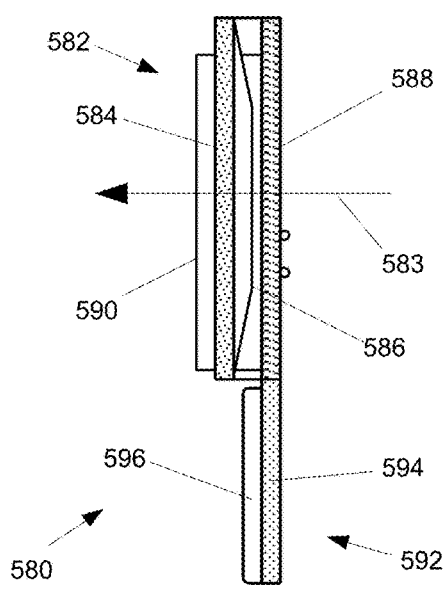
FIG. 27 is a cross-sectional view of another alternative embodiment of a module for use with a facemask having integrated modules in accordance with principles of the invention.

FIG. 27 shows another alternative embodiment of a module 580 in accordance with the principles of the invention. Module 580 also includes an upper region 582 having an outer air filter 584 and a check valve 586 limiting airflow to an outward direction 583. The inner surface of the module is hydrophobic and includes a plurality of ribs 588. Heatsink fins 590 extend from the ribs 588 and protrude from the outer air filter 584 to draw heat away from the hydrophobic inner surface. The lower region 592 includes a receptacle 594 for collecting the condensed saliva/liquid. An indicator strip 596 is located on the outer surface of the lower region 592 and changes color when a substance is detected in the collected saliva.

Figure 28:
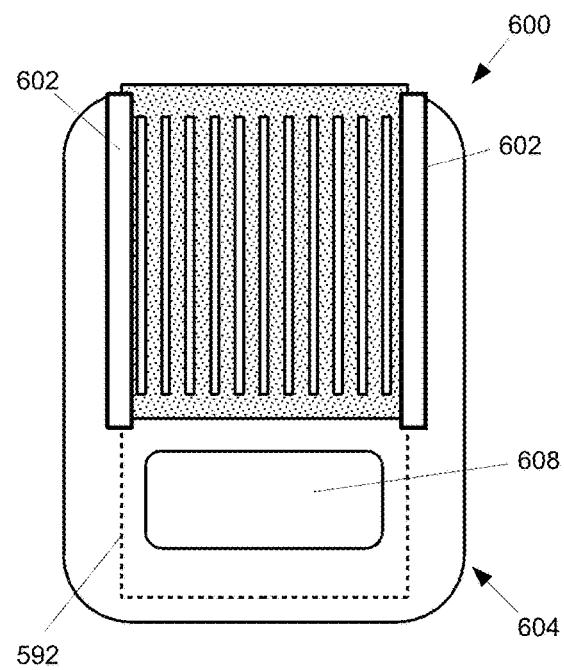
FIG. 28 is an outside view of another alternative embodiment of a module attached to a socket for use with a facemask having integrated modules in accordance with principles of the invention.

FIG. 28 shows another alternative embodiment of a socket 600 in accordance with the principles of the invention. Socket 600 is similar to socket 560 and includes U-shaped channels 602 and a lower air impermeable region 604 for housing the lower region 592 of the module 580. A transparent window 608 extends over the air impermeable region 604, and allows people within the vicinity of the wearer to review the color of the indicator strip 596, thereby informing them of whether the substance has been detected in the wearer saliva.

Figure 29:
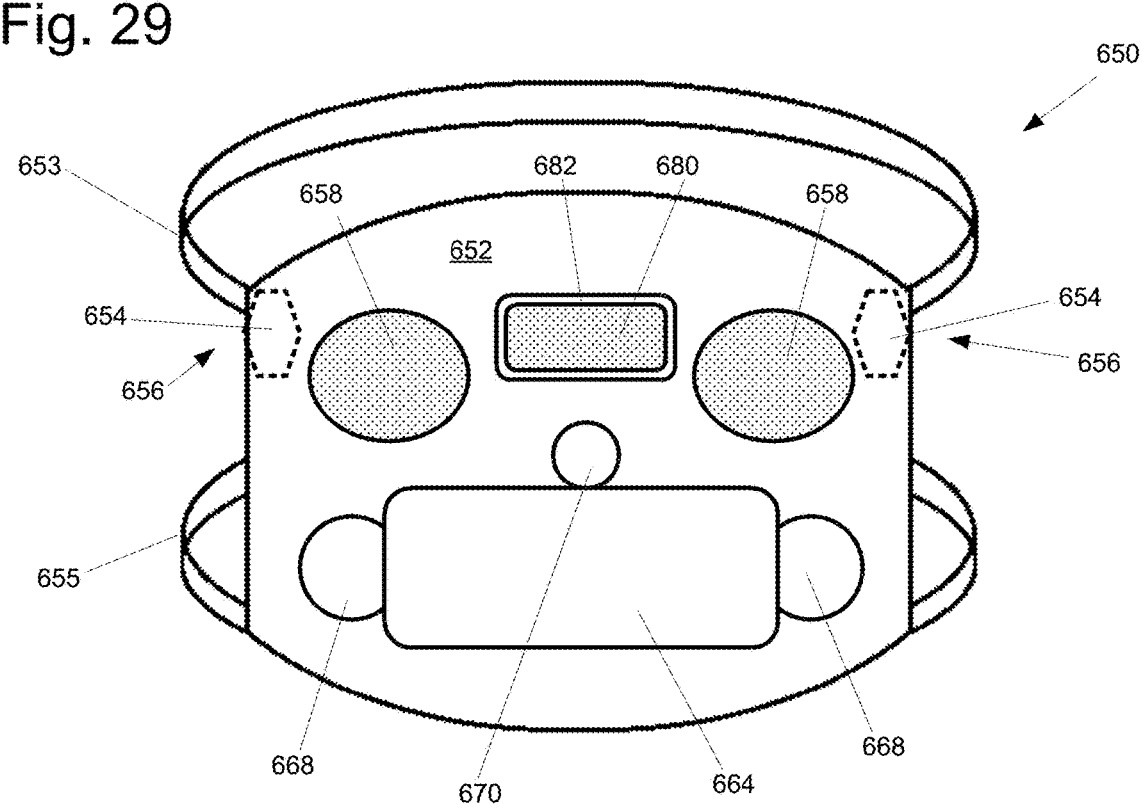
FIG. 29 is an outside view of another alternative embodiment of a facemask having integrated modules in accordance with principles of the invention.
Figure 30:
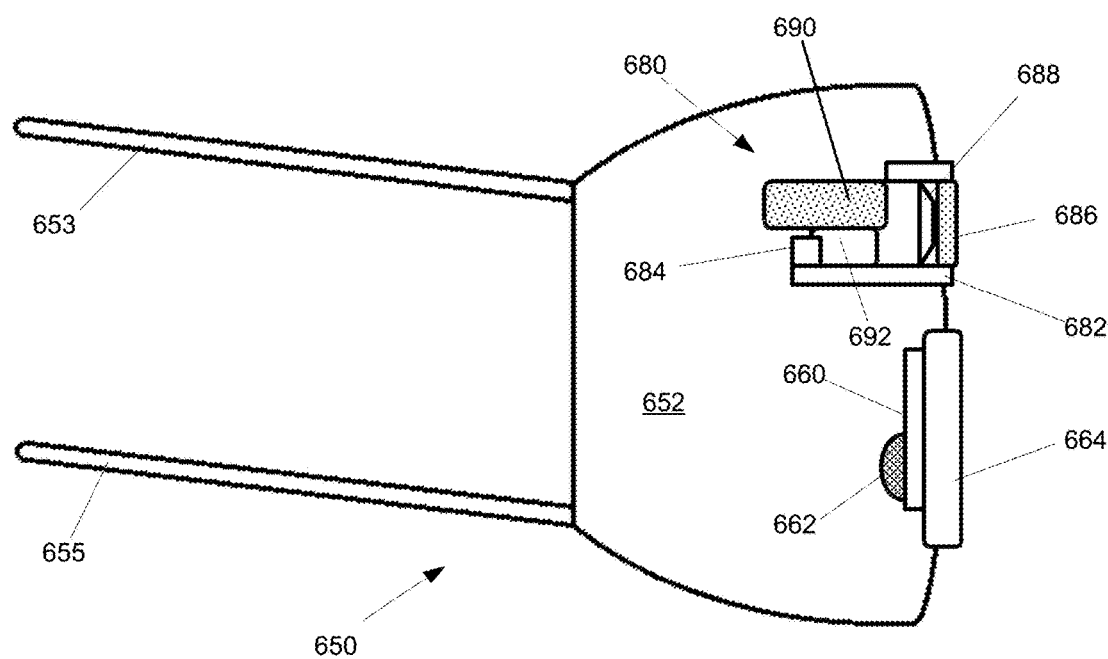
FIG. 30 is a side cut-away view of another alternative embodiment of a facemask having integrated modules in accordance principles of the invention.
Figure 31:
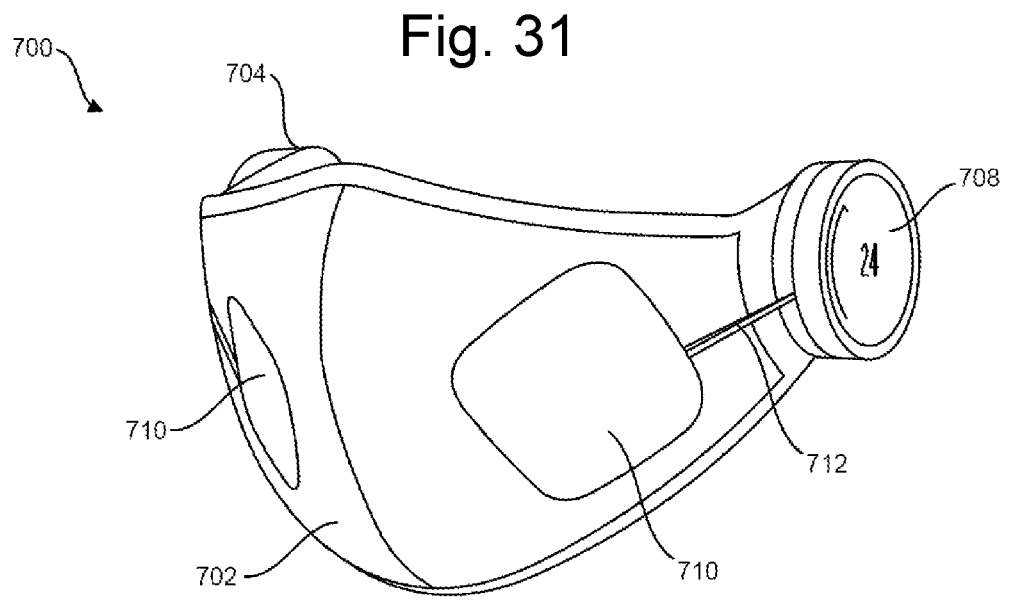
FIG. 31 is a perspective view of another alternative embodiment of a facemask having integrated modules in accordance with principles of the invention.
Figure 32:
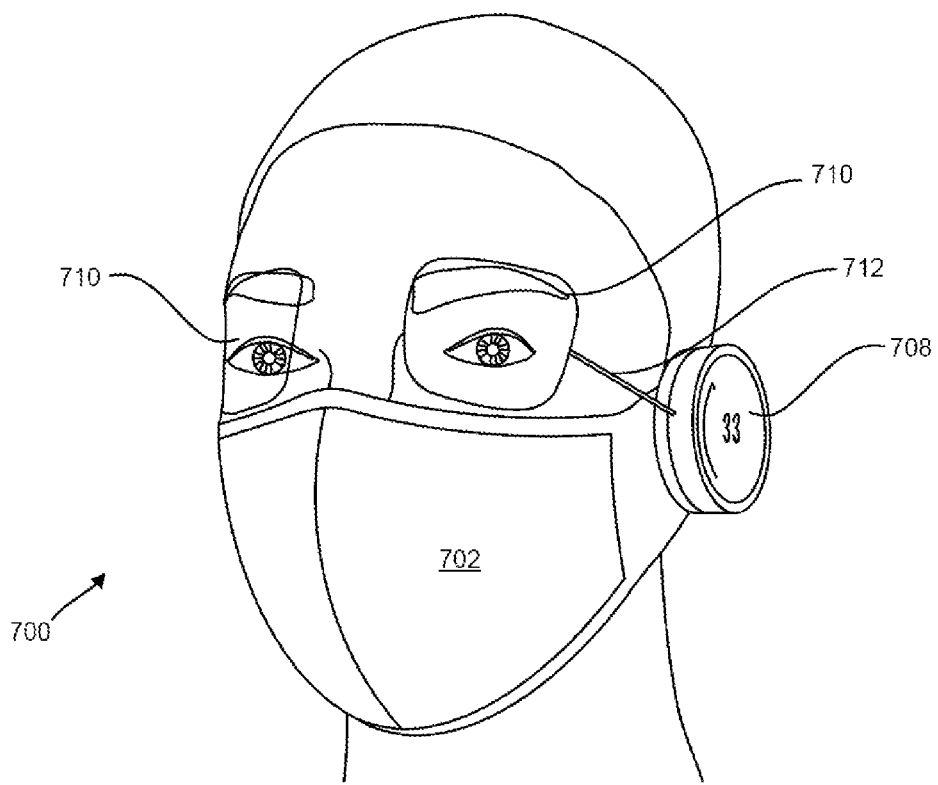
FIG. 32 is another perspective of another alternative embodiment of a facemask having integrated modules being worn by a person in accordance principles of the invention.
Figure 33:
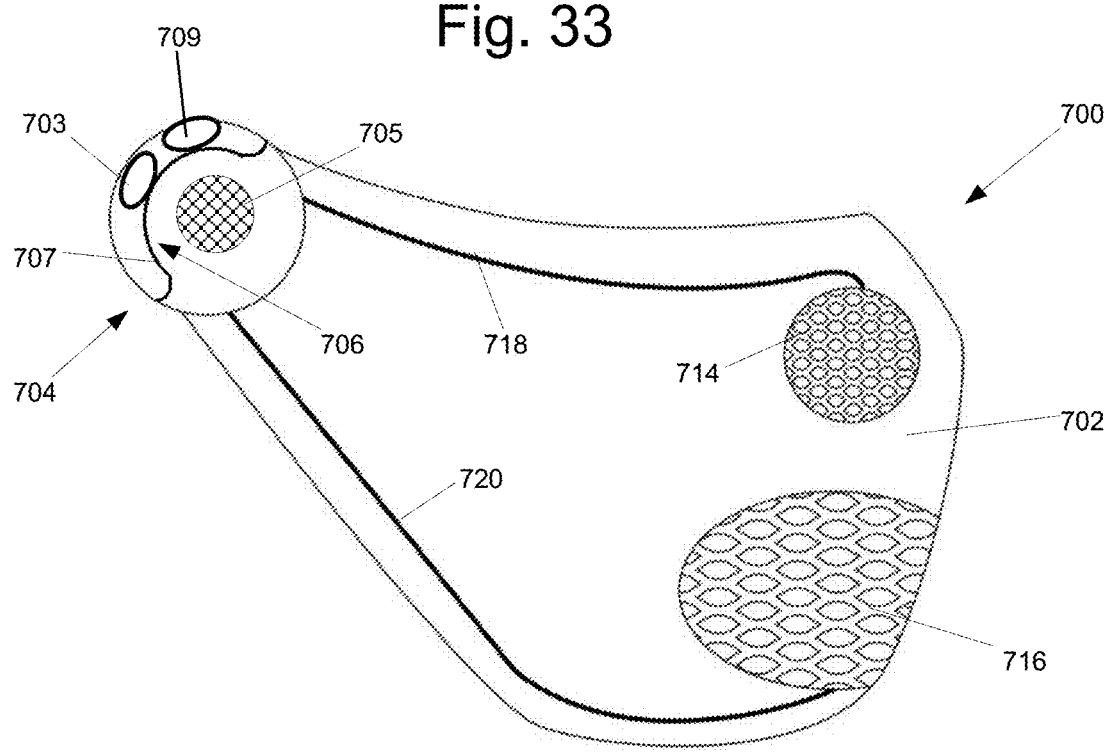
FIG. 33 is a side cut-away view of another alternative embodiment of a facemask having integrated modules in accordance principles of the invention.

FIGS. 29 and 30 show another alternative embodiment of a facemask 650 in accordance with principles of the invention. This embodiment includes various functionalities and mechanisms that may be added to a facemask in general and its various components will be understood by a skilled artisan as being capable of being incorporated into any of the other facemasks described herein. Facemask 650 is formed from a panel 652 of flexible material and held in place covering a wearer's nose and mouth by two bands 653 and 655 configured to wrap around the wearer's head. The bands may be elastic or may optionally be adjustable as is well known in the art. A skilled artisan will also appreciate that a single band may be used or additional bands may optionally be included. The panel 652 may also optionally be incorporated into a helmet, hat or other headgear. The panel 652 includes two heart rate and temperature sensors 654 in each of its upper corners 656. The panel 652 also includes two exhalation filter modules 658 that limit airflow to the outward direction and filter the exhaled air to prevent spreading of a communicable disease. The modules 658 are similar to like modules described above and may be permanently incorporated into the panel 652 or may be interchangeable. They may also include a turbine for generating electricity. The facemask 650 includes a microcontroller 660 having a microphone 662 and a relatively large video screen 664. It also includes speakers 668. The microcontroller 660 may include software or programming allowing it to translate between languages. The wearer may speak into the microphone 662 and the microcontroller 660 will translate what the wearer speaks into a different language. This different language translation may be displayed on the video screen 664 and/or emitted by the speakers 668 so that people within the wearer's vicinity may hear the wearer's translated message. This may be particularly helpful when the wearer is in a different and unfamiliar country. In addition, the facemask 650 may also include a still or video camera 670 that may record or transmit still images or video. This feature may be useful when the wearer is a police officer, a soldier, an athlete or otherwise partaking in an activity where a video recording is desirable.

Facemask 650 also includes another alternative embodiment of a module 680. The modules described above have all been substantially flat and configured to more or less conform to the mask itself. Module 680 is configured to extend substantially farther inside the facemask than these previously described modules, and specifically to extend underneath the wearer's nose. It is snapped into a socket 682 which includes an electrical communication port 684. The module 680 includes a filter 686, a check valve 688 limiting airflow to an inward direction, a compartment 690 containing a material saturated with a medicament or other substance, and its own internal microcontroller 692 for regulating the amount of medicament or other substance aerosolized by the module 680 when the wearer inhales through his or her nose. Those skilled in the art will appreciate that some substances are preferably administered through a person's nose rather than inhaled directly. For example, sinus medication is typically intended to be inhaled through the nose. Optionally, the compartment 690 may include a scented air freshener for use when the wearer encounters a foul smell. For example a wearer inside a chicken rendering plant or sewer system will undoubtedly wish to avoid the unpleasant smells found in those environments. The module 680 may be used to mask and/or filter those unpleasant smells. Module 680 may also be used to administer any substances that are readily absorbed by nasal passages.

FIGS. 31-34 show another alternative embodiment of a facemask 700 having integrated modules in accordance with principles of the invention. Facemask 700 includes a panel 702 configured to fit over a wearer's nose and mouth. The facemask 700 includes at least one microcontroller 708 covering one of the earpieces 704. In this embodiment, there are two microcontrollers 708, one positioned over each of the earpieces 704. Facemask 700 also includes two optical head mounted displays 710, each connected to its respective the microcontroller 708 by a rotatable arm 712. The optical head mounted displays 710 project an image in the wearer's line of sight when its respective rotatable arm 712 is rotated into an upward position. Optionally, the optical head mounted display 710 may be merely protective eye coverings that do not project an image. The optical head mounted displays 710 may be used to provide information to the wearer. The wearer may also use the optical head mounted display 710 to review text messages, emails and other electronic documents.

The two opposing earpieces 704 of this embodiment each include both a heart rate/blood pressure monitor 703 and a thermometer 709 located on a curved lip 707. The lip 707 forms a channel 706 configured to fit over and around a wearer's ear, thus securing the mask in place on a wearer. Because the curved lip 707 extends over the top of the earlobe, it provides a well-suited location for both the heart rate monitor 703 and the thermometer 709. Those skilled in the art will appreciate that other locations are also suitable. The two opposing earpieces 704 may also optionally include a speaker 705, which may be used when the facemask 700 is being used as a mobile phone and/or to provide information to the wearer. For example, the speaker 705 may used to provide an audio signal to the wearer. The audio signal may be something as simple as repeated beeping to inform the wearer that a sensor integrated into the facemask 700 has detected a particular object, such as a virus or bacteria, within the wearer's exhaled breath. Optionally, an audio signal may be used to advise the wearer that he or she has reached or exceeded a desired maximum level of exertion, blood pressure, and/or respiratory activity.

The facemask 700 also includes a nose module 714 and a mouth module 716. One or both of these modules may be removably incorporated into a socket on the panel 702. The modules 714 and 716 are in communication with at least one of the microcontrollers 708 via the nose module wire 718 and the mouth module wire 720. One or both modules 714 and 716 may include a check valve, sensors and/or a filter, as described above. Optionally, the nose module 714 may be configured only to dispense aerosolized substances as also described above and may also optionally be configured to not allow air to pass through it in either the inward or outward direction.

Figure 35:
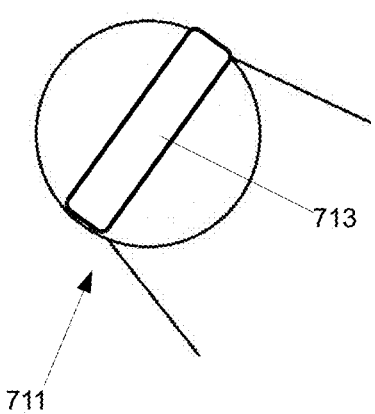
FIG. 35 is a side view of an alternative embodiment of an earpiece of a facemask having integrated modules in accordance with principles of the invention.

FIG. 35 shows an exemplary alternative earpiece 711 in accordance with principles of the invention. Earpiece 711 uses an elastic strap 713 to removably affix to the wearer's ear. Those skilled in the art will appreciate that a variety of mechanisms and/or fasteners may be used to removably attach a mask to the wearer's head. For example, the straps and elastic bands described in previous embodiments would also be suitable for facemask 700. The facemask 700, or any other facemask, could also be combined with a hat or helmet.

Figure 36:
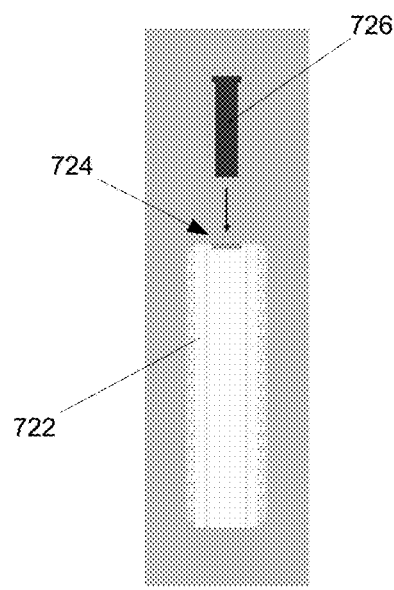
FIG. 36 is a front view of an alternative embodiment of a microcontroller of a facemask having integrated modules in accordance with principles of the invention.
Figure 37:
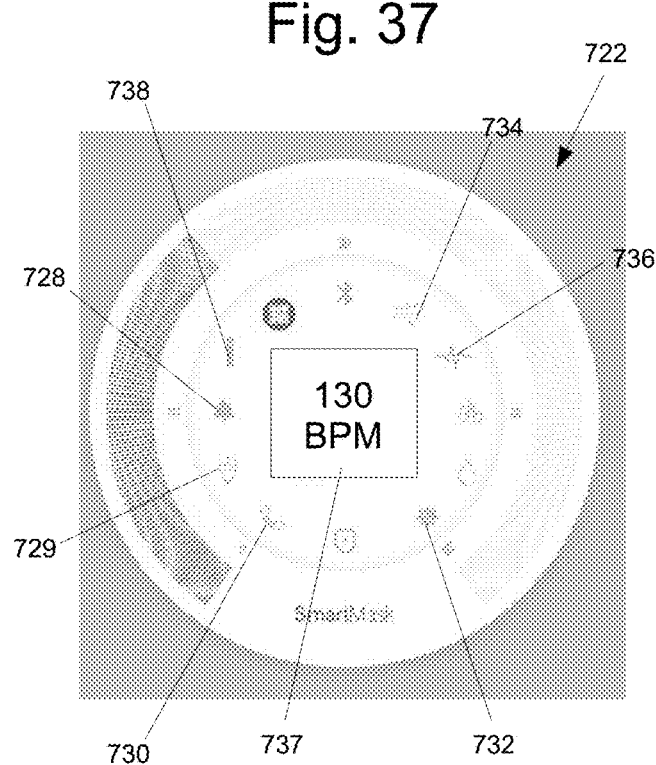
FIG. 37 is a side elevation view of an alternative embodiment of a microcontroller of a facemask having integrated modules in accordance with principles of the invention.

FIGS. 36 and 37 show an exemplary microcontroller 722 having a slot 724 for removably inserting a SIM card 726 or other electronic storage medium. For example, a chip having geographical or cartography data may be inserted into a microcontroller 722 so that it provides maps to the wearer, which may be displayed on the optical display, or may simply be used to provide instructions and/or directions to the wearer when traveling to a predetermined location. The microcontroller 722 also includes several buttons for programming different features. The alert button 728 is used to program alerts and reminders. The GPS button 729 informs the wearer of his or her current location when depressed. The phone button 730 may be used to activate the phone features of the facemask 700. Other buttons include button 732 for actuating a sensor to detect infectious diseases, button 734 for detecting oxygen levels, button 736 for detecting lung capacity, and button 738 for administering vapor to the wearer. A central display screen 737 displays various information about the wearer, such as his or her heart rate, lung capacity, alerts, and to also indicate whether the wearer is currently on a phone call.

Figure 34:
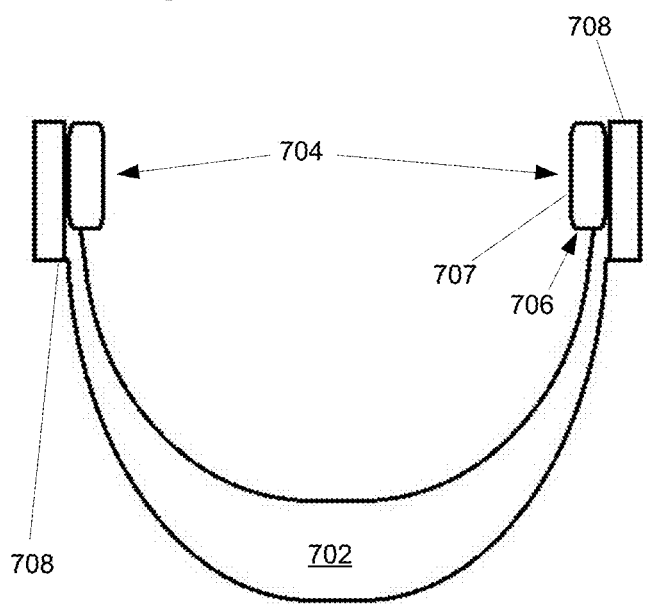
FIG. 34 is a top plan view of another alternative embodiment of a facemask having integrated modules in accordance principles of the invention.
Figure 38:
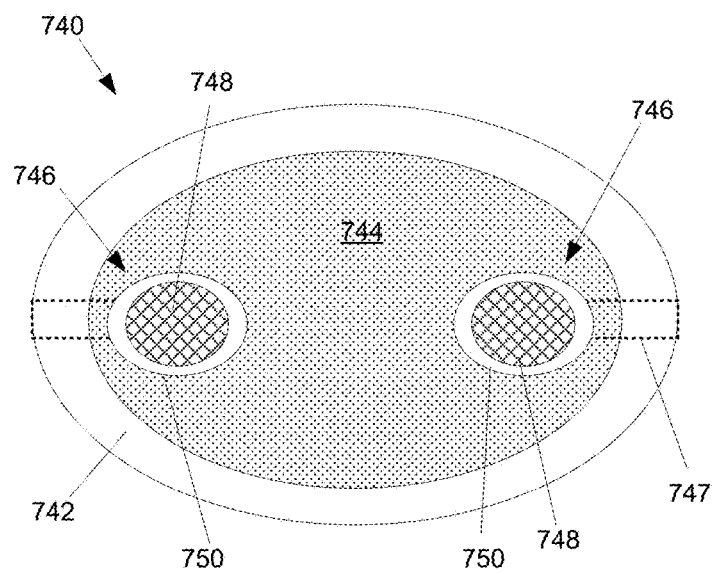
FIG. 38 is an inside view of an alternative embodiment of a module of a facemask having integrated modules in accordance with principles of the invention.
Figure 39:
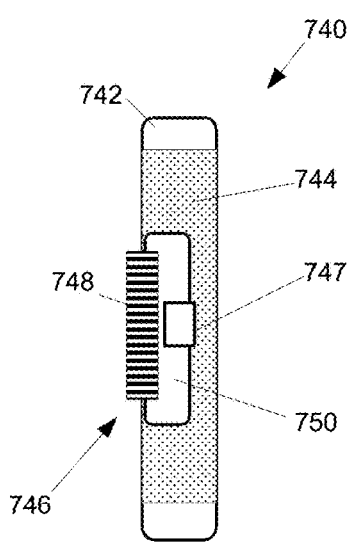
FIG. 39 is a side cross-sectional view of an alternative embodiment of a module of a facemask having integrated modules in accordance with principles of the invention.

FIGS. 38 and 39 show an exemplary mouth module 740 for use with facemask 700 or other facemasks described herein in accordance with principles of the invention. The mouth module 740 includes a frame 742 supporting a filter 744. In this embodiment, two opposing sensors 746 detect the presence of an object of interest, such as an infectious disease. The two opposing saliva sensors 746 may both be used detect the presence of the same object, or may each be configured to detect a different object. Opposing sensors 746 include a plug 747 for attachment to a wire as shown in FIG. 34. Sensors 746 also include a wicking component 748 and an assay component 750 configured to detect a particular object or substance in the wearer's saliva. To test for the presence of a particular object or substance, the wearer applies saliva tongue to the wicking component 748, for example with his or her tongue. The wicking component 748 is comprised of a plurality of wicking channels that pull the saliva to the assay component 750. The mouth module 740 may optionally not include a wicking component 748 such that the wearer's tongue directly contacts the assay component 750.

Figure 40:
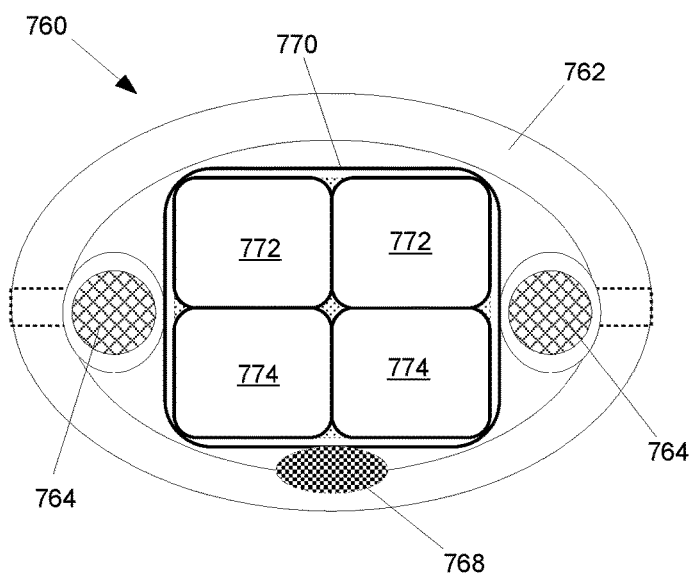
FIG. 40 is an inside view of an alternative embodiment of a module of a facemask having integrated modules in accordance with principles of the invention.
Figure 41:
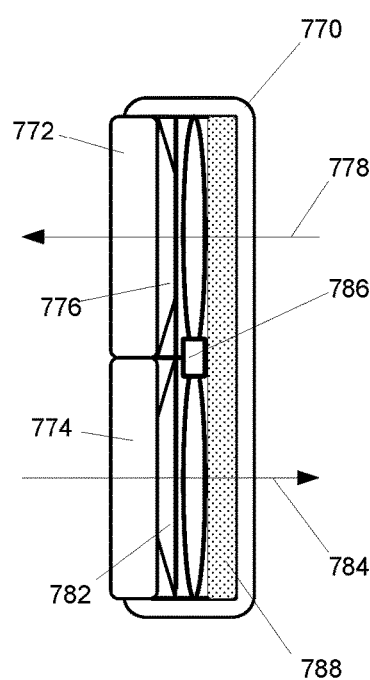
FIG. 41 is a side cross-sectional view of an alternative embodiment of a module in a socket of a facemask having integrated modules in accordance with principles of the invention.

FIGS. 40 and 41 show another exemplary mouth module 760 for use with facemask 700 or other facemasks described herein in accordance with the principles of the invention. Facemask 760 includes a frame 762 with two saliva sensors 764 similar to the saliva sensors 746 described above. The frame 762 also includes a microphone 768, which allows the facemask 700 to function as a cellular phone and also allows the microcontrollers to be voice-activated. Mouth module 760 also includes a socket 770 that may accommodate one or more interchangeable and/or replaceable inhalation sensors 772 and exhalation sensors 774.

FIG. 41 shows a cross-section of the socket 770 housing an inhalation sensor 772 and an exhalation sensor 774. An inhalation check valve 776 only permits airflow through the inhalation sensor 772 in an inward direction 778. Similarly, and exhalation check valve 782 only permits airflow through the exhalation sensor 774 in an outward direction 784. An air flow sensor 786 extends across both the inhalation sensor 772 in the exhalation sensor 774 and may be used to measure the volume and force of both inhaled and exhaled air. The airflow sensor 786 is shown schematically as a fan or turbine blade. Those skilled in the art will appreciate that there are a variety of airflow sensors which will be suitable for use with the present invention. A filter 788 is coextensive with the airflow sensor 786. The inhalation and exhalation sensors 772 and 774, the check valves 776 and 782, and the airflow sensor 786 may all provide information to the microcontrollers 708. If the facemask includes an optical display, some or all of this information may be visually provided to the wearer of the mask. The information may also optionally be provided to the wearer through the speaker in the earpiece. This information may also be transmitted through a wireless network to the wearer's physician, spouse, family or other desired persons.

Figure 42:
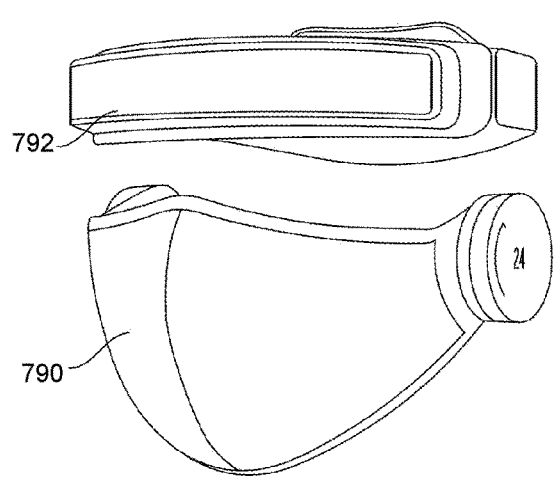
FIG. 42 is a perspective view of another alternative embodiment of a facemask having integrated modules and a visor in accordance with principles of the invention.
Figure 43:
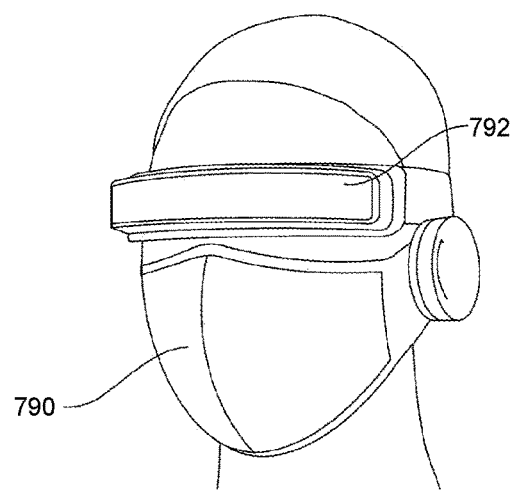
FIG. 43 is a perspective view of another alternative embodiment of a facemask having integrated modules being worn by a person in accordance with principles of the invention.

FIGS. 42 and 43 show another alternative embodiment of a facemask 790 having a visor optical display 792 in accordance with the principles of the invention. The facemask 790 is very similar to the facemask 700, but the optical display takes the form of a visor 792. The visor 792 may be used to convey information to the wearer, to create enhanced reality and/or to function as sunglasses. The visor 792 may optionally be comprised of a material that may be lightened and darkens according to the amount of sunlight present.

Whereas, the present invention has been described in relation to the drawings attached hereto, other and further modifications, apart from those shown or suggested herein, may be made within the spirit and scope of this invention. Those skilled in the art will appreciate that the conception, upon which this disclosure is based, may readily be utilized as a basis for the designing of other structures, methods and systems for carrying out the several purposes of the present invention. Descriptions of the embodiments shown in the drawings should not be construed as limiting or defining the ordinary and plain meanings of the terms of the claims unless such is explicitly indicated. The claims should be regarded as including such equivalent constructions insofar as they do not depart from the spirit and scope of the present invention.

The invention claimed is:

1. A facemask having integrated modules comprising:
   a panel formed from a fabric configured to cover the mouth and nose of a wearer, the panel having an inside surface and an outside surface;
   an air permeable first socket in the panel, wherein air is more likely to flow through the first socket than the fabric;
   a first module removably inserted into the first socket, wherein the first module is configured to detect a presence of a communicable disease in air flowing through the first socket;
   a first check valve restricting airflow through the first socket to an outward direction; and,
   a first filter substantially coextensive with the air permeable first socket and positioned outward relative to the first module;
   wherein the first module comprises an upper section formed from the first filter integrated into an outer layer, an inner moisture capturing layer comprising a plurality of longitudinal hydrophobic ridges, the first check valve located between the outer layer and the inner moisture capturing layer, wherein each of the ridges includes a heat sink fin extending from inside the hydrophobic ridge and through the first check valve and the outer layer; and,
   a lower section comprising an outer layer having a lower check valve limiting airflow to an inward direction through the lower section, and an inner layer comprising a water-soluble inhalable medicament.

2. The facemask having integrated modules of claim 1 further comprising a thermometer.

3. The facemask having integrated modules of claim 2 further comprising a view screen on the facemask is configured to display the temperature measured by the thermometer, and indicate whether the first module has detected the presence of the communicable disease.

4. The facemask having integrated modules of claim 2 further comprising a microphone on the inside surface of the panel, at least one earpiece having a speaker, and a microcontroller providing wireless communication.

5. The facemask having integrated modules of claim 4 further comprising a GPS tracking chip.

6. The facemask having integrated modules of claim 5, wherein the microcontroller is configured to periodically transmit location data obtained from the GPS tracking chip once the first module has detected the presence of the communicable disease.

7. The facemask having integrated modules of claim 6 further comprising a heart rate monitor.

8. The facemask having integrated modules of claim 7 further comprising:
   a second module removably inserted into an air permeable second socket, a second filter substantially coextensive with the second socket; and,
   a second check valve restricting airflow through the second socket to an inward direction.

9. The facemask having integrated modules of claim 8 wherein the first check valve is integrated into the first module and the second check valve is integrated into the second module.

10. The facemask having integrated modules of claim 9 wherein the socket is on the inside of the panel.

11. The facemask having integrated modules of claim 10 further comprising a saliva sensor on the inside surface of the panel.

12. The facemask having integrated modules of claim 11 further comprising at least one airflow sensor.

13. The facemask having integrated modules of claim 12 further comprising an optical head mounted display.

14. The facemask having integrated modules of claim 1 wherein the at least one earpiece comprises two earpieces, each having a lip forming a curved channel configured to fit over a wearer's ear, thereby securing the facemask over the wearer's mouth and nose.

15. The facemask having integrated modules of claim 1 further comprising at least one turbine configured to generate electric power from airflow through at least one air permeable socket.

* * * * *